US006992212B2

(12) United States Patent
Zehner et al.

(10) Patent No.: US 6,992,212 B2
(45) Date of Patent: Jan. 31, 2006

(54) FELXIBLE METHOD FOR THE COMMON PRODUCTION OF FORMIC ACID, A CARBOXYLIC ACID HAVING AT LEAST TWO CARBON ATOMS, AND/OR THE DERIVATIVES OF THE SAME

(75) Inventors: Peter Zehner, Ludwigshafen (DE); Jörg Pastre, Bensheim (DE); Wolfram Stüer, Mannheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 119 days.

(21) Appl. No.: 10/485,622

(22) PCT Filed: Jul. 24, 2002

(86) PCT No.: PCT/EP02/08232

§ 371 (c)(1),
(2), (4) Date: Feb. 3, 2004

(87) PCT Pub. No.: WO03/014053

PCT Pub. Date: Feb. 20, 2003

(65) Prior Publication Data

US 2004/0242924 A1    Dec. 2, 2004

(30) Foreign Application Priority Data

Aug. 7, 2001 (DE) ................. 101 38 778

(51) Int. Cl.
*C07C 67/02* (2006.01)
*C07C 53/02* (2006.01)
*C07C 51/56* (2006.01)

(52) U.S. Cl. .............. 560/234; 562/609; 562/891
(58) Field of Classification Search ............ None
See application file for complete search history.

(56) References Cited

U.S. PATENT DOCUMENTS

| | | |
|---|---|---|
| 2,045,739 A | 6/1936 | Wiezevich |
| 3,328,439 A | 6/1967 | Hamilton |
| 3,787,485 A | 1/1974 | Fernandez |
| 4,002,678 A | 1/1977 | Naglieri et al. |
| 4,018,816 A | 4/1977 | Onoda et al. |
| 4,112,235 A * | 9/1978 | Schmerling ........... 560/1 |
| 4,239,698 A | 12/1980 | Isshiki et al. |
| 4,333,885 A | 6/1982 | Feitler |
| 4,358,411 A | 11/1982 | Porcelli et al. |
| 4,374,070 A | 2/1983 | Larkins et al. |
| 4,430,273 A | 2/1984 | Erpenbach et al. |
| 4,519,956 A * | 5/1985 | Lin et al. ............. 562/519 |
| 4,559,183 A | 12/1985 | Hewlett |
| 4,959,498 A | 9/1990 | Luft et al. |
| 4,978,778 A | 12/1990 | Isshiki et al. |
| 5,003,104 A | 3/1991 | Paulik et al. |

FOREIGN PATENT DOCUMENTS

| | | |
|---|---|---|
| DE | 24 41 502 | 5/1975 |
| DE | 27 10 630 | 9/1978 |
| DE | 28 44 371 | 4/1979 |
| DE | 28 36 084 | 3/1980 |
| DE | 30 24 353 | 1/1981 |
| DE | 35 06632 | 8/1986 |
| EP | 048 174 | 9/1982 |
| EP | 087 870 | 9/1983 |
| EP | 193 799 | 9/1986 |
| EP | 336 218 | 10/1989 |
| EP | 348 309 | 12/1989 |
| EP | 479 463 | 4/1992 |
| EP | 677 505 | 10/1995 |
| GB | 1 365 351 | 9/1974 |
| GB | 2013184 | 8/1979 |
| GB | 2 333 773 | 9/1999 |
| WO | 82/01704 | 5/1982 |
| WO | 93/04026 | 4/1993 |

OTHER PUBLICATIONS

U1.Ency.Ind.Chem,6thEd.2000, Elec.Rel. Formic Acid.
U1.Ency.Ind.Chem.6thEd.2000,Elec.Rel. Actic Acid.
U1.Ency.Ind.Chem.6thEd.2000,Elec Rel. Acetic Anhydride and mixed fatty acid anhyudrides.
U1.Ency.Ind.Chem.6thEd.2000,Elec.Rel. Vinyl Esters.
Derwent.89-128337/17=SU 1432-048.
U1.Ency. Ind.Chem.6thEd.2000,Elec.Rel. Ketenes.
Derwent 87-209292/30 = J6 2135-445.
Derwent 97-316511/29 = JP 09124544.
Derwent Novel 2, 2, 4, 4-tetra-methyl-cyclobutane-diol mfr. by pyrolysis of isobutyric anhydride to di methyl ketone. . .
Apparatus for the preparation of ketene. . . , Fisher et al., Received Feb. 19, 1953, 1055-1057.
Inorganic Chem. Com. vol. 3, No. 11, Marr et al., 617-619.

* cited by examiner

*Primary Examiner*—Paul A. Zucker
(74) *Attorney, Agent, or Firm*—Novak Druce & Quigg; Jason D. Voight

(57) ABSTRACT

Formic acid and a carboxylic acid having at least two carbon atoms and/or derivatives thereof are prepared jointly by a process in which
 (a) a formic ester (I) is transesterified with a carboxylic acid having at least two carbon atoms (II) to form formic acid (III) and the corresponding carboxylic ester (IV); and
 (b) at least part of the carboxylic ester (IV) formed in step (a) is carbonylated to give the corresponding carboxylic anhydride (V).

11 Claims, 11 Drawing Sheets

FELXIBLE METHOD FOR THE COMMON PRODUCTION OF FORMIC ACID, A CARBOXYLIC ACID HAVING AT LEAST TWO CARBON ATOMS, AND/OR THE DERIVATIVES OF THE SAME

The present invention relates to a process for the joint preparation of formic acid and a carboxylic acid having at least two carbon atoms and/or derivatives thereof, for example carboxylic esters, carboxylic anhydrides or ketenes. In particular, the invention relates to a process for preparing formic acid together with methyl acetate, acetic anhydride, acetic acid, ketene and/or vinyl acetate.

Formic acid is an important compound which has a variety of uses. It is used, for example, for acidification in the production of animal fodder, as preservative, as disinfectant, as auxiliary in the textile and leather industries and as synthetic building block in the chemical industry.

The most important processes for preparing formic acid are mentioned below (cf. Ullmann's Encyclopedia of Industrial Chemistry, $6^{th}$ edition, 2000 electronic release, Chapter "FORMIC ACID—Production").

The industrially most important method of preparing formic acid is hydrolysis of methyl formate and subsequent concentration of the aqueous formic acid solution obtained. Known processes which may be mentioned are the Kemira-Leonard process and the BASF process. A great disadvantage of these processes is the formation of an aqueous formic acid solution as a result of the hydrolysis step which leads to a series of further disadvantages. Thus, costly concentration of the formic acid solution by extractive rectification using an entrainer is necessary. Due to the presence of water, the aqueous or concentrated formic acid solution to be handled is extremely corrosive and requires the use of expensive materials of construction for the relevant parts of the plant. The processes mentioned thus have the disadvantages of high capital and operating costs, a technically complicated and elaborate production plant, a high energy consumption and the existence of a not inconsiderable residual water content in the concentrated formic acid.

The oxidation of hydrocarbons, for example butanes or naphtha, forms a broad range of products including formic acid which can be separated off and concentrated in a complicated manner. A disadvantage of this method, too, is the need for extractive rectification of the crude formic acid using an entrainer. Mention may also be made of the abovementioned disadvantages resulting from the water content.

In an older process, formic acid is prepared by hydrolysis of formamide which can be obtained by ammonolysis of methyl formate using ammonia. Hydrolysis is carried out by means of sulfuric acid and water. Disadvantages of this process are the undesirable formation of ammonium sulfate as coproduct and the presence of water, which leads to the abovementioned disadvantages.

Carboxylic acids such as acetic acid and its higher molecular weight homologues are important compounds having a wide variety of uses. They are used, for example, for the preparation of esters, carboxylic anhydrides, as additives in the polymer sector or as intermediates in the preparation of textile chemicals, dyes, plastics, agrochemicals and pharmaceuticals. The low molecular weight homologues acetic acid and propionic acid are of particular importance.

The most important processes for preparing acetic acid and its higher molecular weight homologues are mentioned below (cf. Ullmann's Encyclopedia of Industrial Chemistry, $6^{th}$ edition, 2000 electronic release, Chapter "ACETIC ACID—Production" and Chapter "CARBOXYLIC ACIDS, ALIPHATIC—Production").

The industrially most important method of preparing acetic acid is carbonylation of methanol in the presence of suitable carbonylation catalysts such as carbonyl compounds of cobalt, iridium or rhodium. Known processes which may be mentioned are the BASF process and the Monsanto process. A disadvantage of these processes is the presence of water in the reaction medium, which, as a result of the water gas shift reaction of water and carbon monoxide to form carbon dioxide and hydrogen, reduces the yield of desired product obtained from the carbon monoxide used. Furthermore, a high energy input is necessary in the work-up by distillation because of the water content. Furthermore, the processes mentioned suffer from high capital and operating costs and a technically complicated and elaborate production plant.

The oxidation of hydrocarbons such as ethane, butanes or naphtha forms a broad range of products including acetic acid and possibly its higher homologues which are costly to separate off and concentrate. Mention may also be made of the abovementioned disadvantages resulting from the water content.

The synthesis of carboxylic acids by oxidation of the corresponding aldehydes is based on expensive olefin as starting material. Thus, acetaldehyde is obtained industrially by oxidation of ethene using the Wacker process and its higher homologues are obtained by hydroformylation of ethene, propene, etc. These processes therefore have an economically unattractive raw material basis.

Carboxylic esters, in particular methyl acetate, are important solvents. Methyl acetate is used, for example, for dissolving nitrocellulose or acetylcellulose. Vinyl acetate is widely used in the preparation of polymers and copolymers.

There are many processes for preparing carboxylic esters (cf. Ullmann's Encyclopedia of Industrial Chemistry, $6^{th}$ edition, 2000 electronic release, Chapter "ESTERS, ORGANIC—Production"). Mention may be made of the esterification of carboxylic acids with alcohols, the reaction of carboxylic acid chlorides or carboxylic anhydrides with alcohols, the transesterification of carboxylic esters, the reaction of ketenes with alcohols, the carbonylation of olefins using carbon monoxide and alcohols, the condensation of aldehydes, the alcoholysis of nitriles and the oxidative acylation of olefins.

Alkyl acetates are obtained mainly by esterification of acetic acid or acetic anhydride with alkanols. Methyl acetate is also formed as a by-product in the synthesis of acetic acid (cf. Ullmann's Encyclopedia of Industrial Chemistry, $6^{th}$ edition, 2000 electronic release, Chapter "ACETIC ACID—Production"). A further possible method of synthesizing methyl acetate is the carbonylation of dimethyl ether (cf. Ullmann's Encyclopedia of Industrial Chemistry, $6^{th}$ edition, 2000 electronic release, Chapter "ACETIC ANHYDRIDE AND MIXED FATTY ACID ANHYDRIDES—Acetic Anhydride—Production"). A disadvantage of the latter process is the use of expensive dimethyl ether.

Vinyl acetate is obtained by addition of acetic acid onto ethyne (acetylene), by addition of acetic anhydride onto acetaldehyde and subsequent cleavage of the ethylidene diacetate formed or by oxidative acylation of ethene by means of acetic acid in the presence of oxygen (cf. Ullmann's Encyclopedia of Industrial Chemistry, $6^{th}$ edition, 2000 electronic release, Chapter "VINYL ESTERS—Vinyl Acetate—Production").

GB-A 2 013 184 teaches an integrated process for preparing vinyl acetate from methanol, carbon monoxide and acetaldehyde. In a first step, acetic acid is esterified with methanol to form methyl acetate which is carbonylated in a second step to give acetic anhydride. The acetic anhydride formed is reacted with acetaldehyde in a third step to form, as intermediate, ethylidene diacetate which is subsequently decomposed into vinyl acetate and acetic acid. The acetic acid formed is returned to the first step. A disadvantage of this process is the formation of stoichiometric amounts of water in the esterification step and the associated problems in the handling of water-containing acetic acid and its work-up. A high energy input is necessary in the work-up by distillation to remove the stoichiometric amounts of water formed. In the subsequent carbonylation, the water remaining after the distillation leads to a reduction in the yield of desired product obtained from the carbon monoxide used as a result of the water gas shift reaction of water and carbon monoxide to form carbon dioxide and hydrogen. Furthermore, the processes mentioned suffer from high capital and operating costs and a technically complicated and elaborate production plant.

Acetic anhydride is an important synthetic building block in the chemical industry and is used, for example, for the preparation of acetylcelluloses, acetylsalicylic acid, acetanilide, sulfonamides or vitamin B6.

The most important processes for preparing acetic anhydride are mentioned below (cf. Ullmann's Encyclopedia of Industrial Chemistry, $6^{th}$ edition, 2000 electronic release, Chapter "ACETIC ANHYDRIDE AND MIXED FATTY ACID ANHYDRIDES—Acetic Anhydride—Production").

An industrially important method of preparing acetic anhydride is the reaction of acetic acid with ketene which is obtained in a preceding step by thermal elimination of water from acetic acid. Disadvantages of this process are the very high energy consumption due to the thermal preparation of ketene and the handling of the extremely toxic ketene.

In a further industrially important process for preparing acetic anhydride, methanol is converted by carbonylation and esterification into methyl acetate in a first step and this ester is carbonylated in a second step to form acetic anhydride.

A further method of preparing acetic anhydride is the liquid-phase oxidation of acetaldehyde. A disadvantage of this process is the use of expensive acetaldehyde which is obtained industrially by oxidation of ethene in the Wacker process. This process therefore has an economically unattractive raw material basis.

As a further method of preparing acetic anhydride, mention may be made of the carbonylation of methyl acetate in the presence of a transition metal catalyst. Methyl acetate is generally obtained as a by-product in the synthesis of acetic acid and also by esterification of acetic acid with methanol. EP-A 0 087 870 teaches an integrated process for preparing acetic anhydride and acetic acid from methanol and carbon monoxide. Acetic acid is esterified with methanol in a first step to form methyl acetate which is carbonylated in a second step in the presence of water to give a mixture comprising acetic anhydride and acetic acid. The mixture obtained is worked up by distillation, with the necessary amount of acetic acid being recirculated to the first step. The remaining amount of acetic acid and acetic anhydride is discharged as product. A disadvantage of this process is the formation of stoichiometric amounts of water in the esterification step and the associated problems in the handling of water-containing acetic acid and its work-up. Mention may also be made of the abovementioned disadvantages resulting from the water content.

Ketene is an important, very reactive acylating reagent and is thus an important synthetic building block. The most important industrial use is the preparation of acetic anhydride by reaction with acetic acid.

Ketene is obtained industrially mainly by pyrolysis of acetic acid. This process suffers from the disadvantages of the temperatures required and the high energy consumption associated therewith.

Further processes comprise the thermal decomposition of acetone or acetic anhydride (cf. Ullmann's Encyclopedia of Industrial Chemistry, $6^{th}$ edition, 2000 electronic release, Chapter "KETENES—Ketene—Production").

DETAILED DESCRIPTION OF THE INVENTION

Figure 1:
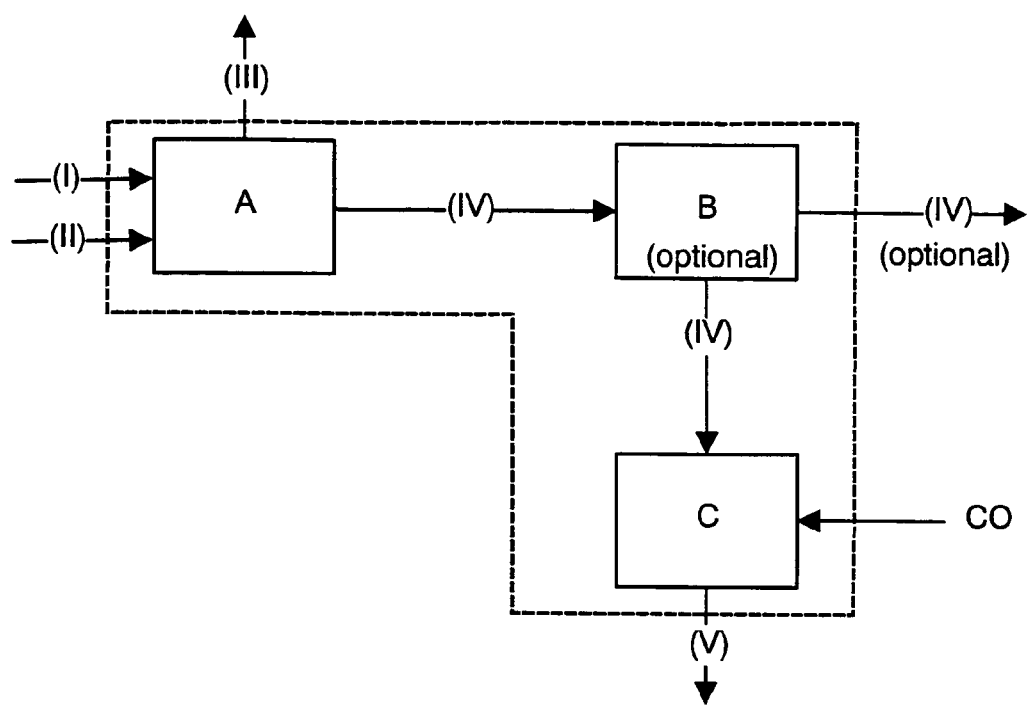
FIG. 1 shows a block diagram of the process of the invention.

It is an object of the present invention to find a process for preparing carboxylic acids and/or derivatives thereof which no longer suffers from the abovementioned disadvantages, has a readily available and economically attractive raw material basis, makes a simple and inexpensive plant possible (low capital costs), avoids undesirable by-products resulting from coupled production and has a low energy consumption and favorable operating costs. A further object is to find a process which, hen required, also makes possible the preparation of anhydrous carboxylic acids and thus allows the handling of less corrosive media and the use of less expensive materials of construction and also offers increasing safety as a result of the reduced corrosivity.

We have found that these objects are achieved by a process for the joint preparation of formic acid and a carboxylic acid having at least two carbon atoms and/or derivatives thereof, wherein a) a formic ester (I) is transesterified with a carboxylic acid having at least two carbon atoms (II) to form formic acid (III) and the corresponding carboxylic ester (IV); and b) at least part of the carboxylic ester (IV) formed in step (a) is carbonylated to give the corresponding carboxylic anhydride (V).

In step (a), a formic ester (I) is reacted with a carboxylic acid having at least two carbon atoms (II) to form formic acid (III) and the corresponding carboxylic ester (IV).

The formic esters to be used have the formula (I)

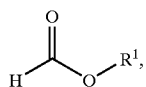

(I)

where the radical $R^1$ is a carbon-containing organic radical. For the purposes of the present invention, a carbon-containing organic radical is preferably an unsubstituted or substituted, aliphatic, aromatic or araliphatic radical having from 1 to 12 carbon atoms which may contain one or more heteroatoms such as oxygen, nitrogen or sulfur, for example in the form of —O—, —S—, —NR—, —CO— and/or —N= in aliphatic or aromatic systems, and/or be substituted by one or more functional groups which can contain, for example, oxygen, nitrogen, sulfur and/or halogen atoms, for example by fluorine, chlorine, bromine, iodine and/or a cyano group.

Formic esters can generally be obtained via a base-catalyzed carbonylation of the corresponding alcohols and also by esterification of the corresponding alcohols with formic acid (cf. Ullmann's Encyclopedia of Industrial Chemistry, 6$^{th}$ edition, 2000 electronic release, Chapter "FORMIC ACID—Derivatives"). The simplest representative of this class of compounds, viz. methyl formate, is obtained industrially by carbonylation of methanol.

For the purposes of the present invention, a carboxylic acid having at least two carbon atoms (II) is a carboxylic acid in which the carboxyl group is attached to a radical having at least one carbon atom. The carboxylic acids to be used have the formula (II)

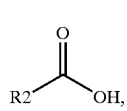

(II)

where the radical $R^2$ is a carbon-containing organic radical as defined in the case of $R^1$.

The abovementioned transesterification reaction in step (a) is an equilibrium reaction which is generally catalyzed by the presence of a catalyst.

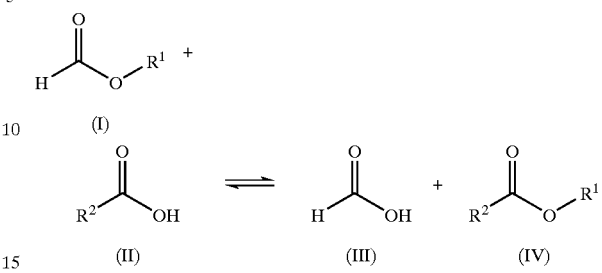

In the process of the present invention, step (a) can be carried out using the known methods of transesterification (cf. Ullmann's Encyclopedia of Industrial Chemistry, 6$^{th}$ edition, 2000 electronic release, Chapter "ESTERS, ORGANIC—Chemical Properties" and "ESTERS, ORGANIC—Production" and the references cited).

As catalysts, use is generally made of small amounts of acidic or basic substances. Preference is given to the use of acids and acidic solids. Examples which may be mentioned are strong protic acids such as sulfuric acid, perchloric acid, benzenesulfonic acid, p-toluenesulfonic acid, molybdophosphoric acid and tungstosilicic acid; acid ion exchangers such as ion exchangers containing perfluorinated sulfonic acid groups (SU-A 1,432,048); and acidic oxides such as zeolites (DE-A 35 06 632), aluminosilicates (U.S. Pat. No. 3,328,439) or $SiO_2/TiO_2$ (DE 27 10 630). Preferred catalysts are mineral acids, p-toluenesulfonic acids and zeolites.

If strong protic acids are used as homogeneous catalysts, their concentration in the reaction mixture is generally from 0.01 to 50% by weight, preferably from 0.01 to 2% by weight.

As cocatalyst in addition to the abovementioned catalysts, it is possible to use water or methanol, generally in an amount of up to 20% by weight, based on the reaction solution. However, it should also be noted that an increase in the water content also leads to an increase in the corrosivity of the reaction medium and makes the work-up of the products more difficult. It may therefore be advantageous to carry out the transesterification without addition of water as cocatalyst. If the transesterification is carried out in the presence of water or methanol, it may be advantageous to add carboxylic anhydride (V) to the reaction product mixture to bind the water. This may be added, for example, directly at the reactor outlet or in the column (eg bottom of column). This measure makes it possible to prepare anhydrous formic acid and an anhydrous carboxylic ester (IV) even in a transesterification which has been cocatalyzed using water or methanol. Thus anhydrous formic acid and anhydrous carboxylic ester (IV) may be prepared without any problems, even when using methanol-containing methyl formate as formic ester (I). When using methyl formate as formic ester (I), the typical residual methanol content of from about 2 to 4% by weight in this ester is found to be advantageous due to its ability to act as cocatalyst.

The transesterification can be carried out either in the liquid phase or in the gas phase. In the case of a transesterification in the gas phase, preference is given to using heterogeneous catalysts such as the abovementioned ion exchangers or acidic oxides. In the case of a transesterification in the liquid phase, homogeneous or heterogeneous catalysts are used. The transesterification is preferably carried out in the liquid phase.

The transesterification is generally carried out at from 20 to 300° C., preferably from 50 to 180° C. The pressure is generally from 0.1 to 5 MPa abs.

The transesterification can be carried out in the presence of an additional inert, polar solvent. For the purposes of the present invention, inert solvents are solvents which do not react chemically with the compounds present, i.e. the starting materials, the products and the catalysts, under the reaction conditions employed. Suitable solvents are, for example, polyethers. Solvents are generally used in transesterifications in which starting materials and/or products which are only insufficiently soluble in the solvent-free reaction mixture at the desired temperature, the desired pressure and the desired ratios of the starting materials and products are present. If the starting materials and products are also soluble in the solvent-free reaction mixture under the conditions chosen, the transesterification is preferably carried out without addition of a solvent.

The starting materials formic ester (I) and carboxylic acid (II) are generally added in stoichiometric amounts.

A nonstoichiometric ratio of the two starting materials can be set deliberately in the reaction mixture by additional addition of one of the two starting materials, for example as an initial charge prior to commencement of the reaction. Thus, for example, a starting material which has good solvent properties can improve the solubility of the other starting material or of the products. It is likewise possible to maintain an appropriate excess of one of the two products in the reaction mixture.

The transesterification can be carried out batchwise or continuously. Preference is given to a continuous process.

The transesterification in the process of the present invention can in principle be carried out using all reaction apparatuses known for transesterification reactions. As suitable reaction apparatuses for a reaction in the liquid phase, mention may be made, for example, of stirred tank reactors, distillation columns, reactive columns and membrane reactors. To achieve a high conversion, it is advantageous for at least one of the two products, preferably both, to be removed continually from the reaction mixture. When using a stirred tank reactor, this is achieved by, for example, continuously taking off the reaction mixture, subsequently separating off the two products and returning the two unreacted starting materials, with or without the catalyst, to the reactor. When using a distillation column, the transesterification reaction takes place in the liquid phase, with the relatively low-boiling components being able to be separated off by distillation and, depending on whether the component is a starting material or product, either returned to the reaction zone or discharged. When using a reactive column, the preferably heterogeneous catalyst is located in the separation region of the column. The relatively low-boiling components are in this case separated off by distillation in a manner similar to that described for the distillation column and are returned to the reaction zone or discharged.

Examples of suitable reaction apparatuses for a reaction in the gas phase are flow tubes or shaft reactors.

The reaction mixture can be separated in various ways. The method employed is generally determined by the properties of the starting materials and products to be separated. Examples of possible separation processes are distillation, crystallization and extraction. It should be pointed out that combinations of various separation methods are also possible, including the case of a distillation column or reactive column upstream of the transesterification. Preference is generally given to separation by distillation, which may also be carried out as a distillation under reduced pressure or a vacuum distillation. If separation by distillation is not possible or possible only with great difficulty, for example in the case of relatively high-boiling or readily decomposable components, the abovementioned alternative methods become important. Given a knowledge of the starting materials, products and any catalyst present, a person skilled in the art can readily develop a suitable work-up concept.

Due to its good distillation properties, formic acid (III) is generally removed by distillation.

In the preferred separation of the resulting reaction mixture by distillation, use is generally made of three distillation columns or their equivalents (e.g. one dividing wall column and one distillation column) to achieve separation into four streams. The stream comprising formic ester (I) is generally returned to the transesterification, the stream comprising the carboxylic ester (IV) is partly or wholly passed to the carbonylation step (b), the formic acid (III) is discharged from the system as product and the remaining stream comprising the carboxylic acid (II) is generally likewise returned to the transesterification.

Since in the following carbonylation of the carboxylic ester (IV) to the carboxylic anhydride (V) any formic ester (I) still present is isomerized in the presence of the carbonylation catalyst to form the corresponding carboxylic acid $R^1$—COOH, it may be possible in a variant having a simplified work-up by distillation with saving of a distillation column to obtain not only a stream comprising formic ester (I), a stream comprising formic acid (III) and a stream comprising carboxylic acid (II) but also, as a further stream, a stream comprising formic ester (I) and carboxylic ester (IV) and to pass this to the carbonylation step (b). This latter stream can, for example, be obtained from a side offtake on the first distillation column.

In the process of the present invention, all of the carboxylic ester (IV) obtained or only part thereof can be passed to the carbonylation step (b). In the latter variant, part of the carboxylic ester (IV) formed can be obtained as end product. The remaining part of the carboxylic ester (IV) is passed to the carbonylation step (b).

In step (b), at least part, preferably at least 5%, particularly preferably at least 10% and very particularly preferably at least 50%, of the carboxylic ester (IV) formed in step (a) is carbonylated in the presence of a catalyst to form the corresponding carboxylic anhydride (V). It is also possible for the total amount of carboxylic ester (IV) formed in step (a) to be carbonylated in step (b).

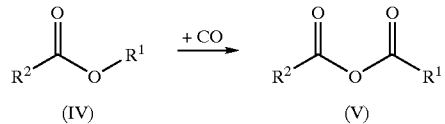

In step (b) of the process of the present invention, it is possible to use the known methods of carbonylating carboxylic esters (cf. Ullmann's Encyclopedia of Industrial Chemistry, 6$^{th}$ edition, 2000 electronic release, Chapter "ACETIC ANHYDRIDE AND MIXED FATTY ACID ANHYDRIDES—Acetic Anhydride—Production" and the references cited).

Catalysts used are generally metals of groups 8 to 10 of the Periodic Table and their compounds in the presence of halides or organic halogen compounds. Preferred catalyst metals are rhodium, iridium, palladium, nickel and cobalt, in particular rhodium (EP-A 0 677 505). Halides and organic halogen compounds used are generally iodine compounds. Preference is given to the addition of alkali metal iodides and alkaline earth metal iodides (U.S. Pat. No. 5,003,104, U.S. Pat. No. 4,559,183), hydroiodic acid, iodine, iodoalkanes, in particular iodomethane (methyl iodide) (GB A 2,333,773, DE-A 24 41 502) or substituted azolium iodide (EP-A 0 479 463). The catalyst metals are generally stabilized by ligands. Preferred ligands are nitrogen and phosphorus compounds such as N-containing heterocyclic compounds (DE-A 28 36 084), amines, amides (DE-A 28 44 371) and phosphines (U.S. Pat. No. 5,003,104, EP-A 0 336 216). The catalyst systems may further comprise promoter metals, for example chromium in the system nickel/chromium (U.S. Pat. No. 4,002,678), ruthenium in the system iridium/ruthenium (GB-A 2,333,773) or cobalt in the system ruthenium/cobalt (U.S. Pat. No. 4,519,956). Preferred catalyst systems are systems comprising rhodium and/or iridium, methyl iodide, nitrogen- and/or phosphorus-containing ligands and, if desired, promoters such as lithium or chromium. Particular preference is given to using a catalyst based on rhodium triiodide, lithium iodide and iodomethane, as described, for example, in U.S. Pat. No. 4,374,070.

The catalyst can be used in unsupported form as a homogeneous catalyst or in supported form as a heterogeneous catalyst. Suitable support materials are, for example, inorganic oxides such as silicon dioxide or aluminum oxide (EP-A 0 336 216), or polymers such as ion exchangers (J6 2135 445) or resins (JP 09 124 544).

The carbonylation can be carried out in the presence of hydrogen (U.S. Pat. No. 5,003,104, GB-A 2 333 773, U.S. Pat. No. 4,333,885, WO 82/01704) or in the absence of hydrogen (A. C. Marr et al., Inorg. Chem. Comm. 3, 2000, pages 617 to 619). It is generally advantageous to carry out the carbonylation in the presence of hydrogen, in which case the hydrogen concentration chosen generally ranges from the ppm range to 15% by volume and is preferably from 1 to 10% by volume, based on the gaseous feed stream.

The carbonylation can be carried out either in the gas phase (EP-A 0 336 216) or in the liquid phase. When it is carried out in the gas phase, supported catalysts are generally used. In the process of the present invention, the carbonylation is preferably carried out in the liquid phase.

A carbonylation in the gas phase is generally carried out at from 130 to 400° C., preferably from 150 to 280° C., and a pressure of from 0.1 to 15 MPa abs, preferably from 0.5 to 3 MPa abs. A carbonylation in the liquid phase is generally carried out at from 100 to 300° C., preferably from 170 to 200° C., and a pressure of from 0.1 to 15 MPa abs, preferably from 1 to 8 MPa abs.

In the case of the preferred carbonylation in the liquid phase and the use of a homogeneous catalyst, a catalyst concentration in the range from 0.01 to 1% by weight, based on the reaction solution, is generally employed.

The carbonylation can be carried out in the presence of an additional inert solvent. For the purposes of the present invention, inert solvents are solvents which do not react chemically with the compounds present, i.e. the starting materials, the products and the catalysts, under the reaction conditions employed. Suitable inert solvents are, for example, aromatic and aliphatic hydrocarbons and also carboxylic acids or their esters. Solvents are preferably used in carbonylations in which the starting material and/or the product is only insufficiently soluble in the solvent-free reaction mixture at the desired temperature and/or the desired pressure. If the starting materials and the products are also soluble in the solvent-free reaction mixture under the conditions chosen, the carbonylation is preferably carried out without addition of a solvent.

The carbonylation can be carried out batchwise or continuously. Preference is given to a continuous carbonylation.

The carbonylation in the process of the present invention can in principle be carried out using all reaction apparatuses known for carbonylation reactions. The carbonylation in the gas phase is generally carried out in a flow tube or shaft reactor. Reaction apparatuses suitable for the preferred carbonylation in the liquid phase are, for example, stirred tank reactors, jet loop reactors and bubble columns. Their use in a continuous process is described briefly below.

When using the abovementioned reaction apparatuses, the desired amounts of carboxylic ester (IV) and carbon monoxide are generally fed continuously into the reaction solution comprising, in particular the carboxylic anhydride (V), the carbonylation catalyst and, if desired, an additional solvent with intensive mixing. The resulting heat of carbonylation can be removed, for example, by means of internal heat exchangers, by cooling the wall of the reaction apparatus and/or by continuously taking off the hot reaction solution, cooling it externally and returning it to the reactor. When using a jet loop reactor or a bubble column, an external circuit is necessary to ensure mixing. The product is taken off continuously and the carbonylation catalyst is subsequently separated off in a suitable separation apparatus. An example of a suitable separation apparatus is a flush evaporator in which the carboxylic anhydride (V) is vaporized by means of a reduction in pressure. The remaining solution, which contains the carbonylation catalyst, is returned to the reaction apparatus. Appropriate temperature and pressure conditions may also make it possible for the carboxylic anhydride formed to be taken off continuously from the reaction solution by vaporization (DE-A 30 24 353). The vaporized carboxylic anhydride (V) can, depending on requirements, be passed to a work-up step or to a further reaction step. In the case of relatively high-boiling carboxylic anhydrides (V) for which the flash evaporation described is not possible because of their low volatility, the crude reaction product has to be worked up by other means, for example by distillation under reduced pressure, by crystallization or by extraction.

The process parameters and measures to be selected in the process of the present invention are dependent, inter alia, on the nature of the carboxylic ester (IV) used, the carboxylic anhydride (V) formed and the catalyst system chosen and can be determined on the basis of customary technical knowledge.

Depending on the chosen starting materials formic ester (I) and carboxylic acid (II), the carbonylation in step (b) forms a symmetrical or asymmetrical carboxylic anhydride, i.e. the radicals $R^1$ and $R^2$ can be identical or different.

It is also possible to add an alcohol $R^1$—OH or $R^2$—OH to the carboxylic ester (IV) to be carbonylated. The alcohol is then converted into the corresponding carboxylic acid $R^1$—COOH (VIIb) or $R^2$—COOH (II). Such an addition makes it possible to increase the ratio of the carbonylation products $R^2$—COOH (II), carboxylic anhydride (V) and $R^1$—COOH (VIIb) to formic acid (I). Thus, for example, the additional introduction of methanol in the cabonylation of methyl acetate (IV) leads to the formation of acetic acid in addition to acetic anhydride from the carbonylation of the methyl acetate (IV). In addition, it is possible for water, carboxylic ester (IV), formic ester (I) or an ether of the formula $R^1$—O—$R^1$, $R^1$—O—$R^2$ or $R^2$—O—$R^2$ to be additionally added as further component to the carboxylic ester (IV) to be carbonylated.

FIG. 1 shows a block diagram of the process of the present invention. In block "A" (transesterification/separation), formic ester (I) and carboxylic acid (II) are reacted to form formic acid (III) and carboxylic ester (IV). The formic acid (III) which is separated off is discharged as end product. The carboxylic ester (IV) which is separated off is passed via an optional block "B" (discharge of carboxylic ester), in which part of the carboxylic ester (IV) formed can, if desired, be discharged as end product, to block "C" (carbonylation). Here, carbon monoxide is fed in to form carboxylic anhydride (V) which is discharged as end product or can be passed as intermediate to an optional downstream step.

In a preferred embodiment of the process of the present invention, at least part, preferably at least 5%, particularly preferably at least 10% and very particularly preferably at least 50%, of the carboxylic anhydride (V) formed in step (b) is converted into the carboxylic acid (II) in step (c). This can in principle be achieved by all methods which lead to the formation of the carboxylic acid (II). The stated conversion is generally carried out by (i) thermal decomposition, by (ii) hydrolysis, by (iii) use as acylating reagent and/or by (iv) hydrogenation.

The reaction routes mentioned are described in more detail below.

(i) Thermal Decomposition

Thermal decomposition of the carboxylic anhydride (V) to form the corresponding carboxylic acid and a ketene is in principle possible in the case of a carboxylic anhydride (V) which has at least one hydrogen atom in the α position relative to the carboxycarbonyl group. The general reaction equation for the decomposition of the carboxylic anhydride (V) to give the carboxylic acid (II) and a ketene is shown below,

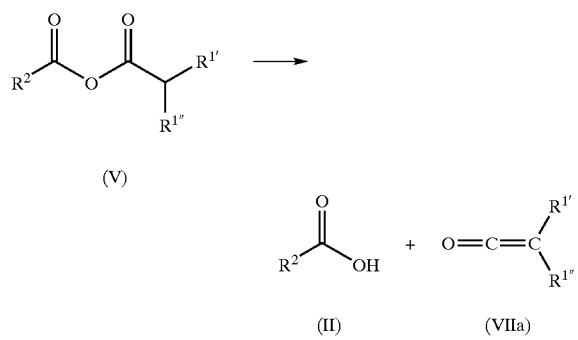

where the radical (R1')(R1")CH comes under the general definition of the radical $R^1$.

A ketene may be regarded as a "monomeric carboxylic anhydride" and is thus encompassed by the term carboxylic acid derivative.

Preference is given to a process for preparing a ketene in which, as a result of appropriate choice of the formic ester (I) and the carboxylic acid (II) in step (a), a symmetrical carboxylic anhydride having at least one hydrogen atom in the α position relative to the carboxycarbonyl group and/or a carboxylic anhydride containing an acetyl group, in particular acetic anhydride, is used as carboxylic anhydride (V) in step (c).

The thermal decomposition can generally be carried out at from 300 to 1000° C., preferably from 350 to 800° C., and a pressure of from 0.01 to 1.0 MPa abs in the gas phase in the presence or absence of a catalyst (cf. U.S. Pat. No. 2,045,739, WO 93/04026 and G. J. Fisher et al., J. Org. Chem. 18, 1954, pages 1055 to 1057). The reaction gas formed, which comprises ketene, carboxylic acid (II), unreacted carboxylic anhydride (V) and by-products such as carbon dioxide or methane, should be cooled as quickly as possible to avoid recombination to form the carboxylic anhydride (V) again.

The specific process parameters and measures to be selected are dependent, inter alia, on the nature of the carboxylic anhydride (V) used, the reaction products formed and any catalyst chosen and can be determined on the basis of customary specialist knowledge.

The gaseous output from the reactor, which comprises the ketene (VIIa), the carboxylic acid (II) and any unreacted carboxylic anhydride (V) and by-products, is, for example, cooled in one or more stages so that the carboxylic acid (II) formed condenses out. The ketene (VIIa) is generally gaseous under these conditions and is discharged in gaseous form.

In another variant, the gaseous output from the reactor is, for example, passed to a scrubbing tower, with the crude reaction product being able to be precooled by means of a cooling zone located upstream of the scrubbing tower. The solvent used in the scrubbing tower preferably corresponds to the carboxylic acid (II) formed. In general, the scrubbing tower is operated so that the carboxylic acid (II) fed in is scrubbed out and the ketene is discharged in gaseous form from the scrubbing tower. In general, an amount of carboxylic acid (II) corresponding to the amount formed is taken continuously from the scrubbing tower.

When a relatively high molecular weight ketene (VIIa) and/or a relatively high molecular weight carboxylic acid (II) are/is formed, condensation of the reaction gases or scrubbing by means of a further solvent is also possible.

(ii) Hydrolysis

Hydrolysis of the carboxylic anhydride (V) forms the corresponding carboxylic acids (VIIb) and (II).

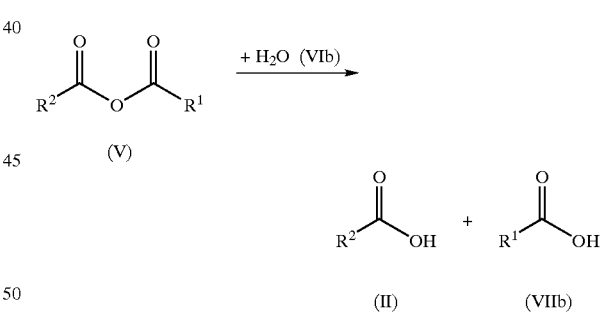

In the process of the present invention, it is possible in principle to use all suitable methods of hydrolyzing carboxylic anhydrides in the hydrolysis in step (c).

The hydrolysis can be carried out in the presence or absence of a catalyst. If strong carboxylic acids, for example acetic acid, are formed by the hydrolysis of the carboxylic anhydride (V), a further catalyst may be able to be dispensed with owing to the catalytic action of the acid(s) formed. On the other hand, if weak carboxylic acids such as butanoic acid (butyric acid) are formed, the addition of a catalyst is generally advisable.

As catalysts, use is generally made of small amounts of acids or acidic solids. In principle, the acids and acidic solids specified for the transesterification in step (a) are also suitable for use in the hydrolysis, and they are hereby expressly incorporated by reference at this point. Preferred catalysts are mineral acids, p-toluenesulfonic acid and zeolites.

If strong protic acids are used as homogeneous catalysts, their concentration in the reaction mixture is generally from 0.001 to 50% by weight, preferably from 0.01 to 10% by weight and particularly preferably from 0.01 to 2% by weight.

The hydrolysis can be carried out either in the liquid phase or in the gas phase. In the case of a hydrolysis in the gas phase, preference is given to using heterogeneous catalysts such as the molecular sieves, ion exchangers or acidic oxides mentioned. In the case of a hydrolysis in the liquid phase, homogeneous or heterogeneous catalysts are used. The hydrolysis is preferably carried out in the liquid phase.

The hydrolysis is generally carried out at from 20 to 300° C., preferably from 50 to 180° C. The pressure is generally from 0.1 to 10 MPa abs, preferably from 0.1 to 5 MPa abs.

The hydrolysis can also be carried out in the presence of an additional inert solvent. For the purposes of the present invention, inert solvents are solvents which do not react chemically with the compounds present, i.e. the starting materials, the products and the catalysts, under the reaction conditions employed. Suitable inert solvents are, for example, those solvents which are described for the transesterification (step (a)).

The starting materials carboxylic anhydride (V) and water (VIb) are generally added in stoichiometric amounts so that the carboxylic anhydride (V) can be reacted completely to form anhydrous carboxylic acids.

The hydrolysis can be carried out batchwise or continuously. Preference is given to continuous hydrolysis.

The hydrolysis in the process of the present invention can in principle be carried out using all reaction apparatuses which make it possible for the reaction solution or the reaction gas to be mixed intensively, are corrosion-resistant under the prevailing acidic conditions and make it possible for the heat of reaction to be removed. A hydrolysis in the gas phase is generally carried out in a flow tube or shaft reactor. Suitable reaction apparatuses for hydrolysis in the liquid phase are, for example, stirred tank reactors, flow tubes provided with mixers, distillation columns and reactive columns. In general, the carboxylic anhydride (V) and the desired amount of water are fed continuously into the reaction apparatus with intensive mixing. Stirred tank reactors and flow tubes are generally provided with appropriate cooling facilities. When a distillation column or reactive column is used, the heat of reaction can advantageously be utilized directly for the distillation. When using an asymmetric carboxylic anhydride (V), it is advantageous to take off one stream comprising carboxylic acid (II) and one stream comprising carboxylic acid (VIIb). When a symmetrical carboxylic anhydride (V) is used, it is usual to take off only one product stream since the carboxylic acids (II) and (VIIb) formed are identical.

When an asymmetric carboxylic anhydride (V) is hydrolyzed in a stirred tank reactor or a flow tube, the reaction product taken off continuously is separated into the carboxylic acids (II) and (VIIb). Any homogeneous catalyst present can generally be returned to the reactor. Examples of possible separation methods are distillation, crystallization and extraction. It should be pointed out that combinations of various separation methods, including installation of a distillation column or reactive column upstream of the hydrolysis, are also possible. Preference is generally given to separation by distillation, which may also be carried out as a distillation under reduced pressure or a vacuum distillation. If separation by distillation is not possible or possible only with great difficulty, for example in the case of relatively high-boiling or readily decomposable components, the alternative methods mentioned become important. Given a knowledge of the properties of the carboxylic acids formed and any catalyst used, a person skilled in the art can readily develop a suitable work-up concept.

In a preferred variant of the process of the present invention, in which the carboxylic acid (II) and the carboxylic acid (VIIb) are obtained by hydrolysis, the carbonylation of step (b) and the hydrolysis of step (c) are carried out together in one reaction apparatus. Suitable reaction apparatuses are in principle all the apparatuses described for the carbonylation in step (b). In this variant, the carboxylic ester (IV), carbon monoxide and water are fed continuously to the reaction apparatus, preferably in a stoichiometric ratio. As catalyst, the reaction mixture contains a carbonylation catalyst as described above. It is also possible and in the case of relatively weak acids generally necessary for the reaction mixture to contain catalytic amounts of a hydrolysis catalyst as described above. Otherwise, the reaction is carried out as described for the carbonylation. The reaction mixture is also taken off and worked up essentially as described for the carbonylation, i.e. preferably by means of a depressurization stage and a flash evaporator from which the products are taken off and the catalyst-containing solution which remains is returned to the reactor. If the carboxylic acids (II) and (VIIb) formed are not identical, the product stream obtained is generally fractionated by customary methods.

It is, of course, also possible to carry out the carbonylation of step (b) and the partial hydrolysis of step (c) together in one reaction apparatus. The amount of water to be added here then depends on the desired proportion of carboxylic acid (VIIb). Thus any mixtures of carboxylic acid (VIIb) and carboxylic anhydride (V) are also obtainable directly as reaction product.

(iii) Use as Acylating Reagent

When the carboxylic anhydride (V) is used as acylating reagent, an acyl group is formally transferred to a suitable hydrogen-active substrate, with the remaining acyloxy group being converted into the carboxylic acid via an intermediate which may be able to be isolated. For the purposes of the present invention, hydrogen-active substrates are compounds which are able to formally transfer a hydrogen radical to the acyloxy group.

Without implying a limitation, a description is given below of reactions (aa) to (ee) in which the carboxylic anhydride (V) can be used as acylating agent so as to form the carboxylic acid (II). It may be pointed out that when an asymmetric carboxylic anhydride (V) is used, acylation generally occurs by means of both the $R^1$—CO— group and the $R^2$—CO— group to form a corresponding carboxylic acid mixture comprising $R^2$—COOH and $R^1$—COOH. In the interests of simplicity, both reaction paths have been summarized in the reaction scheme below. The formulae in the reaction scheme which contain the radical "R1/2" represent a corresponding mixture of compounds containing the radicals $R^1$ and $R^2$.

The reactions (aa) to (ee) below are preferably carried out using a symmetrical carboxylic anhydride (V) since in this case the two radicals $R^1$ and $R^2$ are identical and as a result only one carboxylic acid, namely the carboxylic acid (II), and only one carboxylic acid derivative are formed.

(aa) Reaction with an Alcohol to Form a Carboxylic Ester (VIIc)

The general reaction equation is:

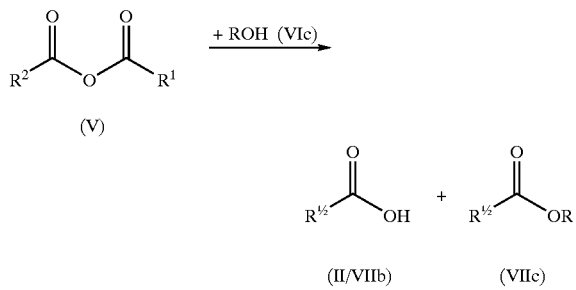

The radical R is generally a carbon-containing organic radical.

The radical R is preferably an unsubstituted or substituted, unbranched or branched, acyclic or cyclic $C_1$–$C_{12}$-alkyl radical such as methyl, ethyl, propyl, 1-methylethyl, butyl, 1-methylpropyl, 2-methylpropyl, 1,1-dimethylethyl, pentyl, hexyl, heptyl, 1-ethylpentyl, octyl, 2,4,4-trimethylpentyl, nonyl, 1,1-dimethylheptyl, decyl, undecyl, dodecyl, phenylmethyl, 2-phenylethyl, 3-phenylpropyl, cyclopentyl, cyclopentylmethyl, 2-cyclopentylethyl, 3-cyclopentylpropyl, cyclohexyl, cyclohexylmethyl, 2-cyclohexylethyl or 3-cyclohexylpropyl for an unsubstituted $C_1$–$C_{12}$-alkyl radical and 2-hydroxyethyl or 2-hydroxypropyl for a substituted $C_1$–$C_{12}$-alkyl radical;

an unsubstituted or substituted, unbranched or branched, acyclic or cyclic $C_2$–$C_{12}$-alkenyl radical such as vinyl (ethenyl), 2-propenyl, 1-methylvinyl, 3-butenyl, cis-2-butenyl, trans-2-butenyl, 3-cyclopentenyl, 2-cyclohexenyl, 3-cyclohexenyl or 2,5-cyclohexadienyl;

an unsubstituted or substituted aromatic radical having one ring or two or three fused rings, where one or more ring atoms may be replaced by heteroatoms such as nitrogen and one or more of the hydrogen atoms may be replaced by substituents such as alkyl or aryl groups; or an oligomeric or polymeric group such as a cellulose radical, a polyvinyl alcohol radical, a sugar radical, a sugar alcohol radical or a glyceryl radical.

Particular preference is given to using an alcohol (VIc) in which the radical R is an unsubstituted, unbranched or branched, acyclic $C_1$–$C_6$-alkyl radical, specifically methyl, ethyl, propyl, 1-methylethyl, butyl, 1-methylpropyl, 2-methylpropyl, 1,1-dimethylethyl, pentyl or hexyl or is the substituted $C_2$-alkyl radical 2-hydroxyethyl. Very particular preference is given to using methanol, ethanol, propanol or butanol.

In the reaction with an alcohol in step (c) of the process of the present invention, it is in principle possible to use all suitable methods of reacting carboxylic anhydrides with alcohols. In general, the reaction is carried out in the presence of a catalyst, and catalysts which can be used are generally any catalysts which are also suitable for catalyzing the transesterification reaction (step (a)). The catalysts described there are hereby incorporated by reference at this point.

The reaction with an alcohol can also be carried out in the presence of an additional inert solvent. For the purposes of the present invention, inert solvents are solvents which do not react chemically with the compounds present, i.e. the starting materials, the products and the catalysts, under the reaction conditions employed. Suitable inert solvents are, for example, those solvents which are described for the transesterification (step (a)).

The manner in which the reaction is carried out, the reaction parameters to be selected, the choice of suitable reaction apparatuses and the work-up and separation of the reaction mixture are very similar to those described for the hydrolysis, which are hereby incorporated by reference at this point.

The specific process parameters and measures to be chosen depend, inter alia, on the nature of the carboxylic anhydride (V) used, the alcohol used, the reaction products formed and the catalyst chosen and can be determined with the aid of customary specialist knowledge.

In the process of the present invention, the use of the carboxylic anhydride (V) as acylating reagent in a reaction with an alcohol to form a carboxylic ester is preferred.

When a diol is used as alcohol (VIc), the corresponding dicarboxylic diester is formed. When the preferred 1,2-ethanediol (glycol) is used, the reaction is as shown in the following equation:

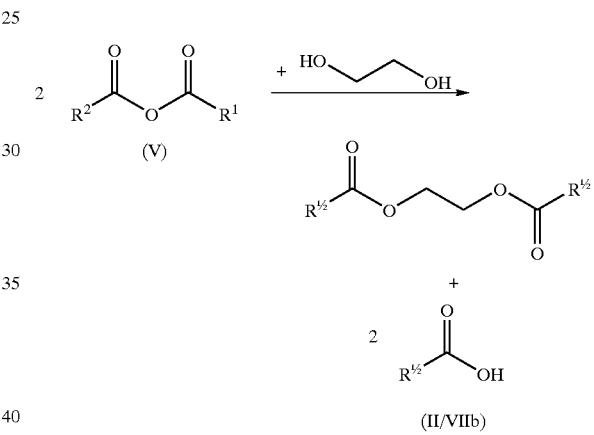

The dicarboxylic diester formed can, for example, be cleaved in a subsequent step to form the corresponding vinyl carboxylate and the carboxylic acid (II/VIIb):

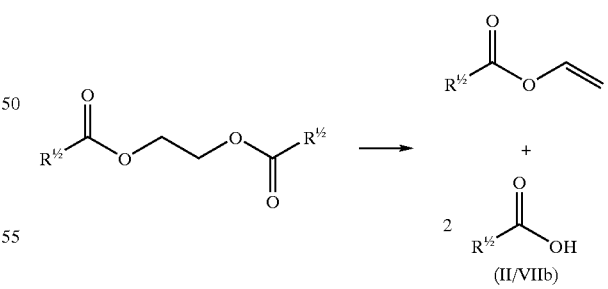

For this cleavage, it is in principle possible to use any methods suitable for this purpose. It is described, for example, in GB-A 1 365 351 and U.S. Pat. No. 3,787,485 and is generally carried out at from 200 to 800° C., preferably from 400 to 600° C., and a pressure of from 0.01 to 1.0 MPa abs in the gas phase in the presence or absence of a catalyst. Suitable reactors for the reaction of the second stage are, for example, flow tubes. The reaction gas formed, which comprises vinyl carboxylate, the carboxylic acid (II), unreacted dicarboxylic diester and by-products such as carbon dioxide or methane, should be cooled as quickly as possible to avoid decomposition and polymerization of the vinyl carboxylate. The reaction products are generally obtained by condensation and/or scrubbing out by means of a suitable solvent, preferably the carboxylic acid (II). In general, further work-up steps such as distillation at elevated temperature and/or under reduced pressure, crystallization or extraction are carried out in a subsequent stage. The type of separation methods used is generally determined by the properties of the starting materials and products to be separated. Given a knowledge of the starting materials, products and any catalyst present, a person skilled in the art can readily develop an appropriate work-up concept. The specific process parameters and measures to be selected can be determined with the aid of customary specialist knowledge.

(bb) Reaction with Ammonia or an Amine to Form a Carboxamide (VIId)

The reaction of the carboxylic anhydride (V) with a secondary amine is shown by way of example:

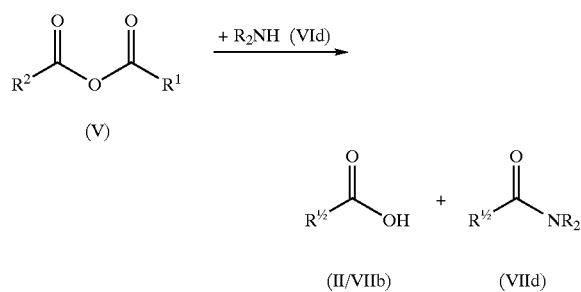

The radical R is generally hydrogen or a carbon-containing organic radical. The radical R is preferably hydrogen;

an unsubstituted or substituted, unbranched or branched, acyclic or cyclic $C_1$–$C_{12}$-alkyl radical such as methyl, ethyl, propyl, 1-methylethyl, butyl, 1-methylpropyl, 2-methylpropyl, 1,1-dimethylethyl, pentyl, hexyl, heptyl, 1-ethylpentyl, octyl, 2,4,4-trimethylpentyl, nonyl, 1,1-dimethylheptyl, decyl, undecyl, dodecyl, phenylmethyl, 2-phenylethyl, 3-phenylpropyl, cyclopentyl, cyclopentylmethyl, 2-cyclopentylethyl, 3-cyclopentylpropyl, cyclohexyl, cyclohexylmethyl, 2-cyclohexylethyl, 3-cyclohexylpropyl or 2-aminoethyl;

an unsubstituted or substituted, unbranched or branched, acyclic or cyclic $C_2$–$C_{12}$-alkenyl radical such as vinyl (ethenyl), 2-propenyl, 1-methylvinyl, 3-butenyl, cis-2-butenyl, trans-2-butenyl, 3-cyclopentenyl, 2-cyclohexenyl, 3-cyclohexenyl or 2,5-cyclohexadienyl;

an unsubstituted or substituted aromatic radical having one ring or two or three fused rings, where one or more ring atoms may be replaced by heteroatoms such as nitrogen and one or more of the hydrogen atoms may be replaced by substituents such as alkyl or aryl groups; or an oligomeric or polymeric group such as a polyvinylamine or a polyethylenimine radical.

Particular preference is given to using a compound of the formula (VId) in which the radicals R are each hydrogen, an unsubstituted, unbranched or branched, acyclic or cyclic $C_1$–$C_6$-alkyl radical, specifically methyl, ethyl, propyl, 1-methylethyl, butyl, 1-methylpropyl, 2-methylpropyl, 1,1-dimethylethyl, pentyl, hexyl and cyclohexyl, or a phenyl radical. Very particular preference is given to using ammonia, dimethylamine or aniline.

The specific process parameters and measures to be selected depend, inter alia, on the nature of the carboxylic anhydride (V) used, the amine used, the reaction products formed and any catalyst employed and can be determined with the aid of customary specialist knowledge.

(cc) Reaction with a Carboxamide to Form an N-acylcarboxamide (VIIe)

The reaction of the carboxylic anhydride (V) with a primary carboxamide is shown by way of example:

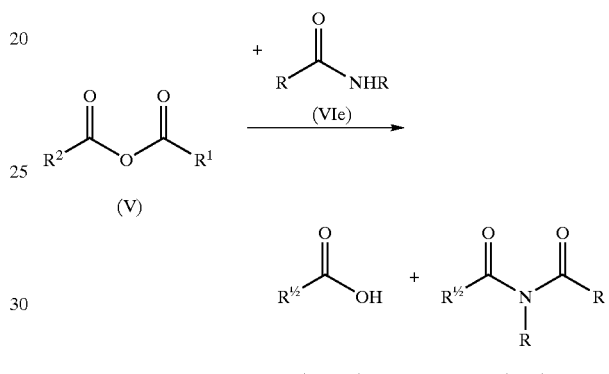

The radical R is generally hydrogen or a carbon-containing organic radical. The radical R is preferably as defined in the case of the amine (VId). Very particular preference is given to using formamide as amide (VIe).

The specific process parameters and measures to be selected depend, inter alia, on the nature of the carboxylic anhydride (V) used, the carboxamide used, the reaction products formed and any catalyst employed and can be determined with the aid of customary specialist knowledge.

(dd) Reaction with an Aldehyde or Ketone to Form an Acylal or Acylone and Cleavage to Form an α,β-unsaturated Carboxylic Ester (VIIf)

The reaction of the carboxylic anhydride (V) with an aldehyde to form an acylal or with a ketone to form an acylone and subsequent cleavage to form an α,β-unsaturated carboxylic ester (VIIf) requires the use of an aldehyde or ketone which has at least one hydrogen atom in the α position relative to the carbonyl group. The general reaction equation for the use of an aldehyde is shown below:

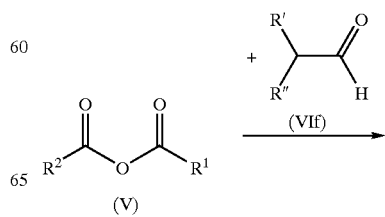

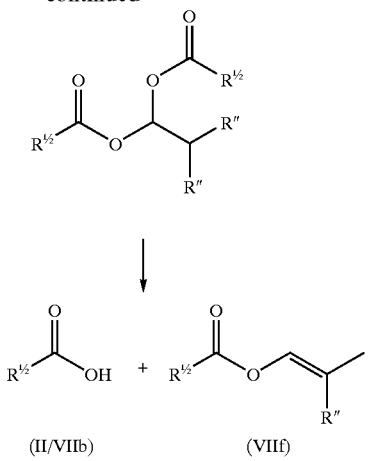

(II/VIIb)    (VIIf)

In the general reaction equation, the radical (R')(R")CH is generally as defined for the radicals $R^1$ and $R^2$. The radical (R')(R")CH is preferably

- an unsubstituted or substituted, unbranched or branched, acyclic or cyclic $C_1$–$C_{12}$-alkyl radical having a hydrogen atom in the α position, for example methyl, ethyl, propyl, 1-methylethyl, butyl, 1-methylpropyl, 2-methylpropyl, pentyl, hexyl, heptyl, 1-ethylpentyl, octyl, 2,4,4-trimethylpentyl, nonyl, 1,1-dimethylheptyl, decyl, undecyl, dodecyl, phenylmethyl, 2-phenylethyl, 3-phenylpropyl, cyclopentyl, cyclopentylmethyl, 2-cyclopentylethyl, 3-cyclopentylpropyl, cyclohexyl, cyclohexylmethyl, 2-cyclohexylethyl or 3-cyclohexylpropyl; or
- an unsubstituted or substituted, unbranched or branched, acyclic or cyclic $C_2$–$C_{12}$-alkenyl radical such as vinyl (ethenyl), 2-propenyl, 1-methylvinyl, 3-butenyl, cis-2-butenyl, trans-2-butenyl, 3-cyclopentenyl, 2-cyclohexenyl, 3-cyclohexenyl or 2,5-cyclohexadienyl.

Particular preference is given to using an aldehyde (VIf) in which the radical (R')(R")CH is an unsubstituted, unbranched or branched, acyclic $C_1$–$C_6$-alkyl radical, specifically methyl, ethyl, propyl, 1-methylethyl, butyl, 1-methylpropyl, 2-methylpropyl, 1,1-dimethylethyl, pentyl and hexyl. Very particular preference is given to using acetaldehyde, propionaldehyde or butyraldehyde or isobutyraldehyde (2-methylpropionaldehyde), in particular acetaldehyde.

As ketone (VIf) preference is given to using acetone (propanone).

As an alternative, it is also possible to use protected aldehydes and ketones, for example acetals or ketals, as described, for example, in J56 040 642.

For the reaction of the carboxylic anhydride (V) to form an α,β-unsaturated carboxylic ester (VIIf), it is in principle possible to use all methods suitable for this purpose. In general, the reaction is carried out in a two-stage process as described, for example, in GB-A 2 013 184.

In the first stage, the carboxylic anhydride (V) is reacted continuously with the aldehyde (VIf) or the ketone in the presence of an acid catalyst, generally in the liquid phase, to form the corresponding addition product. As catalysts, it is generally possible to use any catalysts which are also suitable for catalyzing the transesterification reaction (step (a)). The catalysts described there are hereby incorporated by reference at this point. In general, the first stage of the reaciton is carried out at from 50 to 150° C., preferably from 120 to 140° C. The pressure in the first stage of this reaction is generally unimportant. However, for practical reasons, it should be set so that both the starting materials (V) and (VIf) and also the addition product are predominantly present in the liquid phase. To promote the formation of the addition product, use is generally made of an excess of carboxylic anhydride (V). In general, the molar ratio of (V):(VIf) in the reaction mixture is from 1 to 40. Suitable reactors for the reaction of the first stage are, for example, stirred tank reactors, flow tubes, shaft reactors or jet loop reactors.

As an alternative, the first stage of the reaction to form the addition product can also be carried out in the gas phase in the presence of a heterogeneous catalyst.

The reaction solution is generally taken continuously from the first stage and passed to the second stage for cleavage into the carboxylic acid (II/VIIb) and the α,β-unsaturated carboxylic ester (VIIf). The cleavage is described, for example, in GB-A 2 013 184 and EP-A 0 348 309. It is generally carried out in the liquid phase in the presence of an acid catalyst, and suitable catalysts are generally those which are also suitable for catalyzing the transesterification reaction (step (a)). The catalysts described there are hereby incorporated by reference at this point. The second stage of the reaction is generally carried out at from 60 to 200° C., preferably from 100 to 140° C. The pressure in the second stage of this reaction is generally also unimportant. In general, it is in the range from 0.05 to 1 MPa abs. The cleavage is also generally carried out in the presence of an excess of carboxylic anhydride (V), as described for the first stage. Suitable reactors for the reaction of the second stage are, for example, stirred tank reactors, flow tubes, shaft reactors or jet loop reactors.

Both process stages can also be carried out in the presence of an additional inert solvent. For the purposes of the present invention, inert solvents are solvents which do not react chemically with the compounds present, i.e. the starting materials, the products and the catalysts, under the reaction conditions employed. Suitable inert solvents are, for example, those solvents described in the case of the transesterification (step (a)).

The reaction conditions in the second stage are preferably set so that vaporization of the products, the unreacted starting materials, the by-products and/or any solvent used is possible. The vaporized components are subsequently passed to further work-up, preferably likewise by distillation. The residual solution, which contains the catalyst, is returned to the first stage. If vaporization of the two products carboxylic acid (II) and α,β-unsaturated carboxylic ester (VIIf) in the reactor of the second stage is not possible, these are generally separated off in a downstream stage by means of suitable work-up steps, for instance distillation at elevated temperature and/or under reduced pressure, crystallization or extraction. The type of separation processes employed is generally determined by the properties of the starting materials and products to be separated. Given a knowledge of the starting materials, products and any catalyst present, a person skilled in the art can readily develop a suitable work-up concept.

The specific process parameters and measures to be selected depend, inter alia, on the nature of the carboxylic anhydride (V) used, the aldehyde or ketone used, the reaction products formed and the catalyst chosen and can be determined by means of customary specialist knowledge.

In the process of the present invention, the use of a carboxylic anhydride (V) as acylating reagent in a reaction with an aldehyde or ketone to form an α,β-unsaturated carboxylic ester is preferred.

(ee) Reaction with an Aromatic Hydrocarbon to Form an Aromatic Ketone (VIIg)

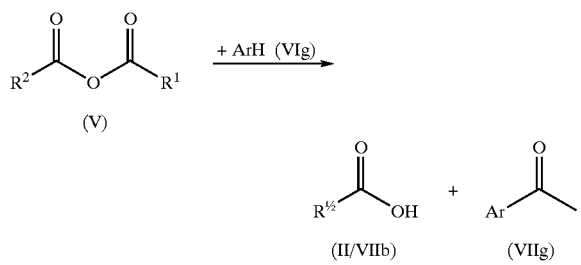

In the general reaction equation, the radical Ar is an unsubstituted or substituted, carbocyclic or heterocyclic aromatic radical preferably having from one to three aromatic rings. Particular preference is given to using benzene, toluene or xylenes as aromatic hydrocarbon.

In the process of the present invention, it is in principle possible to use all suitable methods of acylating aromatic hydrocarbons with carboxylic anhydrides. The specific process parameters and measures to be chosen in the synthesis stage and in the subsequent work-up and separation depend, inter alia, on the nature of the carboxylic anhydride (V) used, the aromatic hydrocarbon used, the reaction products formed and the catalyst selected and can be determined with the aid of customary specialist knowledge.

(iv) Hydrogenation

Hydrogenation of the carboxylic anhydride (V) forms the corresponding aldehyde and the carboxylic acid (II).

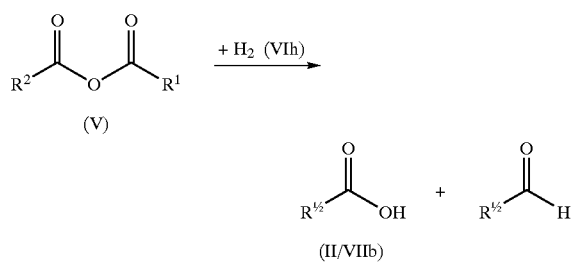

In the process of the present invention, the hydrogenation in step (c) can in principle be carried out using all methods suitable for the hydrogenation of carboxylic anhydrides.

If the radical "R1/2" of the aldehyde formed has a hydrogen atom in the α position relative to the carbonyl group, the reaction generally does not stop at the aldehyde stage, since this reacts preferentially with further carboxylic anhydride to form an acylal. Under suitable reaction conditions, this is cleaved to form an α,β-unsaturated carboxylic ester and the corresponding carboxylic acid (II/VIIb).

Processes for this purpose are known and are described, for example, in U.S. Pat. No. 4,978,778, which is hereby explicitly incorporated by reference. In general, the hydrogenation is carried out using a catalyst system comprising a metal of groups 8 to 10 of the Periodic Table, preferably palladium, rhodium, ruthenium, platinum, osmium, cobalt or nickel, a protic or Lewis acid, preferably an acid selected from among those which are also suitable for the transesterification reaction in step (a), and a halogen-containing compound, preferably a halomethane. The reaction is generally carried out at from 50 to 250° C. and a hydrogen partial pressure of from 0.02 to 10 MPa. It is generally advantageous to carry out the reaction in the presence of carbon monoxide, since this generally increases the catalyst stability and improves the selectivity. The specific process parameters and measures to be selected depend, inter alia, on the nature of the carboxylic anhydride (V) used, the reaction products formed and the catalyst chosen and can be determined with the aid of customary specialist knowledge.

In a preferred variant of the process of the present invention, in which the carboxylic anhydride (V) is converted into the carboxylic acid (II/VIIb) by hydrogenation, the carbonylation of step (b) and the hydrogenation of step (c) are carried out together in one reaction apparatus. A suitable process is described, for example, in EP-A 0 048 174, which is hereby explicitly incorporated by reference. In general, this is carried out using a catalyst system comprising a metal of groups 8 to 10 of the Periodic Table, preferably palladium, rhodium, ruthenium, platinum, osmium, cobalt or nickel, a halogen-containing compound, preferably a halomethane, a nitrogen- or phosphorus-containing promoter, preferably an aliphatic or aromatic amine or a phosphine, and, if desired, a protic or Lewis acid, preferably an acid selected from among those which are also suitable for the transesterification reaction in step (a). The reaction is generally carried out at from 80 to 350° C., preferably from 100 to 250° C., and a hydrogen partial pressure of from 0.3 to 30 MPa. Carbon monoxide and hydrogen are generally introduced in a molar ratio of $CO:H_2$ of from 0.5 to 5. The specific process parameters and measures to be selected depend, inter alia, on the nature of the carboxylic anhydride (V) used, the reaction products formed and the catalyst chosen and can be determined with the aid of customary specialist knowledge.

In a preferred embodiment of the process of the present invention, at least part of the carboxylic acid (II) formed in step (c) is used as starting material in step (a). Preference is given to taking at least 10%, particularly preferably at least 50% and very particularly preferably at least 90%, of the carboxylic acid (II) necessary for the transesterification in step (a) from step (c). In particular, all of the carboxylic acid (II) necessary for the transesterification in step (a) is taken from step (c). To ensure this, product discharge, i.e. the taking of product from the circular process of the present invention, should be such that step (c) produces at least that amount of carboxylic acid (II) which is to be fed to step (a) as recirculated carboxylic acid (II).

Figure 2:
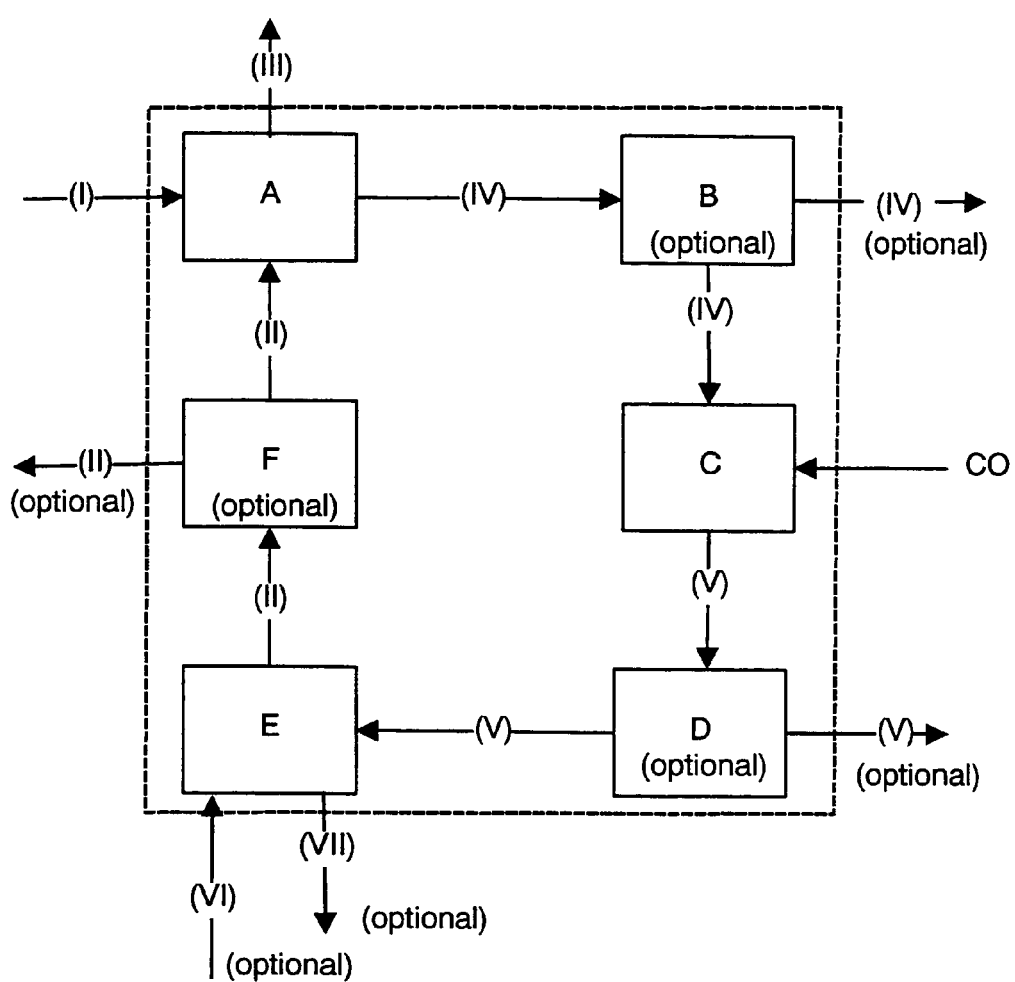
FIG. 2 shows a block diagram of the preferred process of the invention.

FIG. 2 shows a block diagram of the preferred process of the present invention. The blocks "A" to "C" are as described for the block diagram of FIG. 1. The carboxylic anhydride (V) from block "C" (carbonylation) is passed via an optional block "D" (discharge of carboxylic anhydride), in which part of the carboxylic anhydride (V) formed may be discharged as end product, to block "E" (conversion into the carboxylic acid (II)/separation). Depending on the type of conversion reaction chosen, introduction of a starting material (VI) into block "E" may or may not be necessary. The reaction product(s) formed in block "E" is/are the carboxylic acid (II) and, depending on the type of conversion reaction chosen, possibly a further product (VII). The product (VII) which is optionally formed is separated off and discharged as end product. The carboxylic acid (II) is passed via an optional block "F" (discharge of carboxylic acid), in which part of the carboxylic acid (II) formed may be discharged as end product, to block "A" (transesterification/separation).

In the process of the present invention, preference is given to using a formic ester (I)

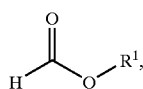

in which the radical $R^1$ is
an unsubstituted or substituted, unbranched or branched, acyclic or cyclic $C_1$–$C_{12}$-alkyl radical such as methyl, ethyl, propyl, 1-methylethyl, butyl, 1-methylpropyl, 2-methylpropyl, 1,1-dimethylethyl, pentyl, hexyl, heptyl, 1-ethylpentyl, octyl, 2,4,4-trimethylpentyl, nonyl, 1,1-dimethylheptyl, decyl, undecyl, dodecyl, phenylmethyl, 2-phenylethyl, 3-phenylpropyl, cyclopentyl, cyclopentylmethyl, 2-cyclopentylethyl, 3-cyclopentylpropyl, cyclohexyl, cyclohexylmethyl, 2-cyclohexylethyl or 3-cyclohexylpropyl; or
an unsubstituted or substituted, unbranched or branched, acyclic or cyclic $C_2$–$C_{12}$-alkenyl radical such as vinyl (ethenyl), 2-propenyl, 1-methylvinyl, 3-butenyl, cis-2-butenyl, trans-2-butenyl, 3-cyclopentenyl, 2-cyclohexenyl, 3-cyclohexenyl or 2,5-cyclohexadienyl.

Particular preference is given to using a formic ester (I) in which the radical $R^1$ is an unsubstituted, unbranched or branched, acyclic $C_1$–$C_6$-alkyl radical, specifically methyl, ethyl, propyl, 1-methylethyl, butyl, 1-methylpropyl, 2-methylpropyl, 1,1-dimethylethyl, pentyl and hexyl. Very particular preference is given to using methyl formate, ethyl formate, propyl formate or butyl formate, in particular methyl formate.

In the process of the present invention, preference is given to using a carboxylic acid (II)

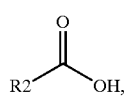

in which the radical $R^2$ is
an unsubstituted or substituted, unbranched or branched, acyclic or cyclic $C_1$–$C_{12}$-alkyl radical such as methyl, ethyl, propyl, 1-methylethyl, butyl, 1-methylpropyl, 2-methylpropyl, 1,1-dimethylethyl, pentyl, hexyl, heptyl, 1-ethylpentyl, octyl, 2,4,4-trimethylpentyl, nonyl, 1,1-dimethylheptyl, decyl, undecyl, dodecyl, phenylmethyl, 2-phenylethyl, 3-phenylpropyl, cyclopentyl, cyclopentylmethyl, 2-cyclopentylethyl, 3-cyclopentylpropyl, cyclohexyl, cyclohexylmethyl, 2-cyclohexylethyl, 3-cyclohexylpropyl, chloromethyl, dichloromethyl, trichloromethyl; or
an unsubstituted or substituted, unbranched or branched, acyclic or cyclic $C_2$–$C_{12}$-alkenyl radical such as vinyl (ethenyl), 2-propenyl, 1-methylvinyl, 3-butenyl, cis-2-butenyl, trans-2-butenyl, 3-cyclopentenyl, 2-cyclohexenyl, 3-cyclohexenyl or 2,5-cyclohexadienyl.

Particular preference is given to using a carboxylic acid (II) in which the radical $R^2$ is an unsubstituted or substituted, unbranched or branched, acyclic $C_1$–$C_6$-alkyl radical, specifically methyl, ethyl, propyl, 1-methylethyl, butyl, 1-methylpropyl, 2-methylpropyl, 1,1-dimethylethyl, pentyl, hexyl, chloromethyl, dichloromethyl or trichloromethyl; or
an unsubstituted, unbranched or branched, acyclic $C_2$–$C_6$-alkenyl radical such as vinyl (ethenyl), 2-propenyl, 1-methylvinyl, 3-butenyl, cis-2-butenyl or trans-2-butenyl.

Very particular preference is given to using acetic acid and propionic acid, in particular acetic acid.

In the process of the present invention, particular preference is given to using formic acid together with methyl acetate, acetic anhydride, acetic acid, ketene, vinyl acetate, ethyl acetate, propyl acetate and/or butyl acetate.

In the process of the present invention, the formic ester (I) and the carboxylic acid (II) are generally used in the transesterification in step (a) in a ratio of 1:1, with the relative concentrations in the reaction mixture being able to deviate therefrom. The carboxylic acid (II) is introduced as fresh starting material, as recirculated stream from step (c) or as a combination of the two. According to the reaction equation

reaction of one mol of formic ester (I) with one mol of carboxylic acid (II) forms one mol of formic acid (III) as product to be taken off and one mol of carboxylic ester (IV). Since at least part of the carboxylic ester (IV) formed in step (a) is carbonylated to form the corresponding carboxylic anhydride (V) in accordance with the reaction equation

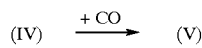

the overall reaction forms one mol of carboxylic ester (IV) and carboxylic anhydride (V) as product to be taken off.

If, according to the preferred process, at least part of the carboxylic anhydride (V) formed in step (b) is converted into the carboxylic acid (II) in accordance with the reaction equation

the overall reaction results in formation of one mol of carboxylic ester (IV), carboxylic anhydride (V) and carboxylic acid derivative (VII) as product to be taken off. In the case of the hydrolysis of a symmetrical carboxylic anhydride (V), one mol of carboxylic anhydride (V) forms two mol of carboxylic acid (II)

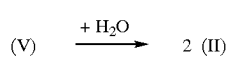

The carboxylic acid (II) formed can be discharged as product or return to the transesterification in step (a).

If the amounts of products to be taken off are chosen appropriately, it is possible without problems to carry out the preferred process with recirculation of the carboxylic acid (II) in such a way that virtually all the carboxylic acid (II) necessary for step (a) comes from the recirculation. Slight losses, for example as a result of selectivities of less than 100% or inadvertent discharge, can be compensated by appropriate additions of carboxylic acid (II). If a symmetrical carboxylic anhydride (V) is formed in the process carried out, as occurs, for example, in the case of the very particularly preferred use of methyl formate (I) and acetic acid (II), the slight losses can be compensated by hydrolysis of the carboxylic anhydride (V) in accordance with the above reaction equation. Table 1 gives an overview of the preferred process variants, with indication of the stoichiometric ratios using the formic acid (III) formed as reference. The last column shows the process blocks required; in the interests of clarity, the optional blocks for the discharge of possible intermediates have not been listed.

Some preferred embodiments are described in more detail below, without implying any restriction.

Embodiment 1: Preparation of Formic Acid and Acetic Anhydride

Figure 3:
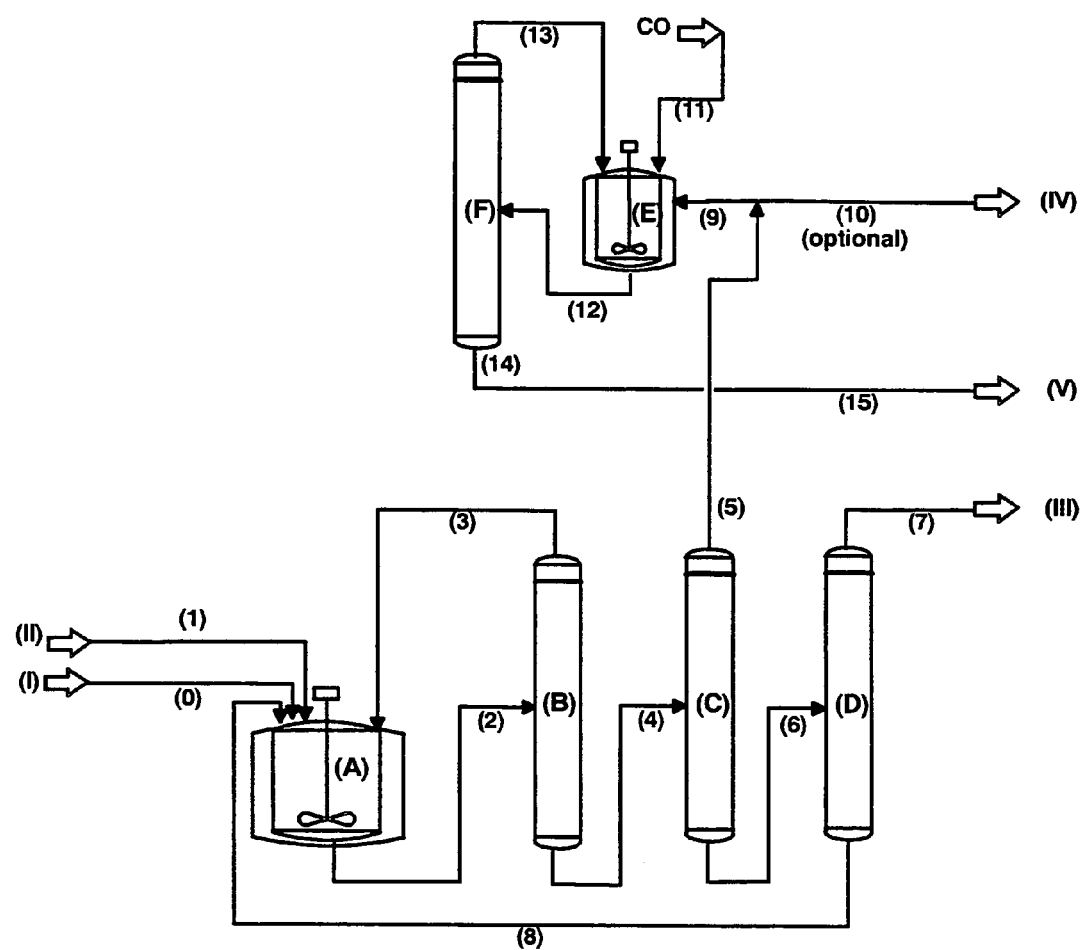
FIG. 3 shows a simplified process flow diagram for preparation of formic acid and acetic anhydride.

A simplified process flow diagram is shown in FIG. 3. Methyl formate (I) and acetic acid (II) are fed continuously to the reactor (A), which is shown by way of example as a stirred tank, via line (0) and (1). However, other suitable reaction apparatuses, for example those described above for step (a), can also be used as reactor (A). In the reactor (A), the transesterification to form formic acid (III) and methyl acetate (IV) takes place in the presence of the catalyst used. The reaction mixture, which comprises methyl formate (I), acetic acid (II), formic acid (III), methyl acetate (IV) and the catalyst used, is taken continuously from the reactor (A) and conveyed via line (2) to the work-up by distillation, which is depicted by way of example in the form of the columns (B), (C) and (D). Unreacted methyl formate (I) and any low boilers formed are returned via line (3) to the reactor (A). Formic acid (III) is taken off via line (7). Unreacted acetic acid (II), catalyst and any high boilers formed are returned to the reactor (A) via line 8. It goes without saying that part of the stream (8) can, if necessary, be discharged continuously or discontinuously to avoid accumulation of high boilers and this can, if desired, be worked up further. Methyl acetate (IV) is passed on via line (5).

It is generally advantageous to employ a separating wall column for the two columns (B) and (C). Stream (3) is then taken off at the top, stream (5) is taken off as a side stream and stream (6) is taken off at the bottom.

The optional line (10) makes it possible to take off methyl acetate (IV) if desired.

Methyl acetate (IV) is fed continuously via line (9) to the reactor (E), generally freed of catalyst, for example in a flash evaporator (not shown in the interests of simplicity), which is shown by way of example as a stirred tank, where it is carbonylated. However, it is also possible to use other suitable reaction apparatuses, for example those described above for step (b), as reactor (E). In reactor (E), carbon monoxide is fed in via line (11) and carbonylation to acetic anhydride (V) takes place in the presence of the catalyst used. The reaction mixture, which comprises unreacted methyl acetate (IV), acetic anhydride (V) and the catalyst used, is taken continuously from the reactor (E) is generally freed of catalyst, for example in a flash evaporator (not shown in the interests of simplicity) and conveyed via line (12) to the work-up by distillation, which is depicted by way of example in the form of the column (F). Unreacted methyl acetate (IV) and any low boilers formed are recirculated via line (13) to the reactor (E). The bottoms from the column (F), which comprise acetic anhydride (V) and any high boilers formed, are taken off via line (14) and are generally separated into acetic anhydride (V) and high boilers in a further column (not shown in the interests of simplicity). The catalyst-containing stream is generally returned to the reactor (E). It goes without saying that part of the stream comprising the high boilers can, if necessary, be discharged continuously or discontinuously to avoid accumulation of high boilers and can be worked up further if desired.

If the stream (12) further comprises acetic acid, for example because of partial hydrolysis as a result of the addition of water, an additional column is generally required to separate off the acetic acid.

Embodiment 2: Preparation of Formic Acid and Methyl Acetate (with Acetic Acid Circuit)

Figure 4:
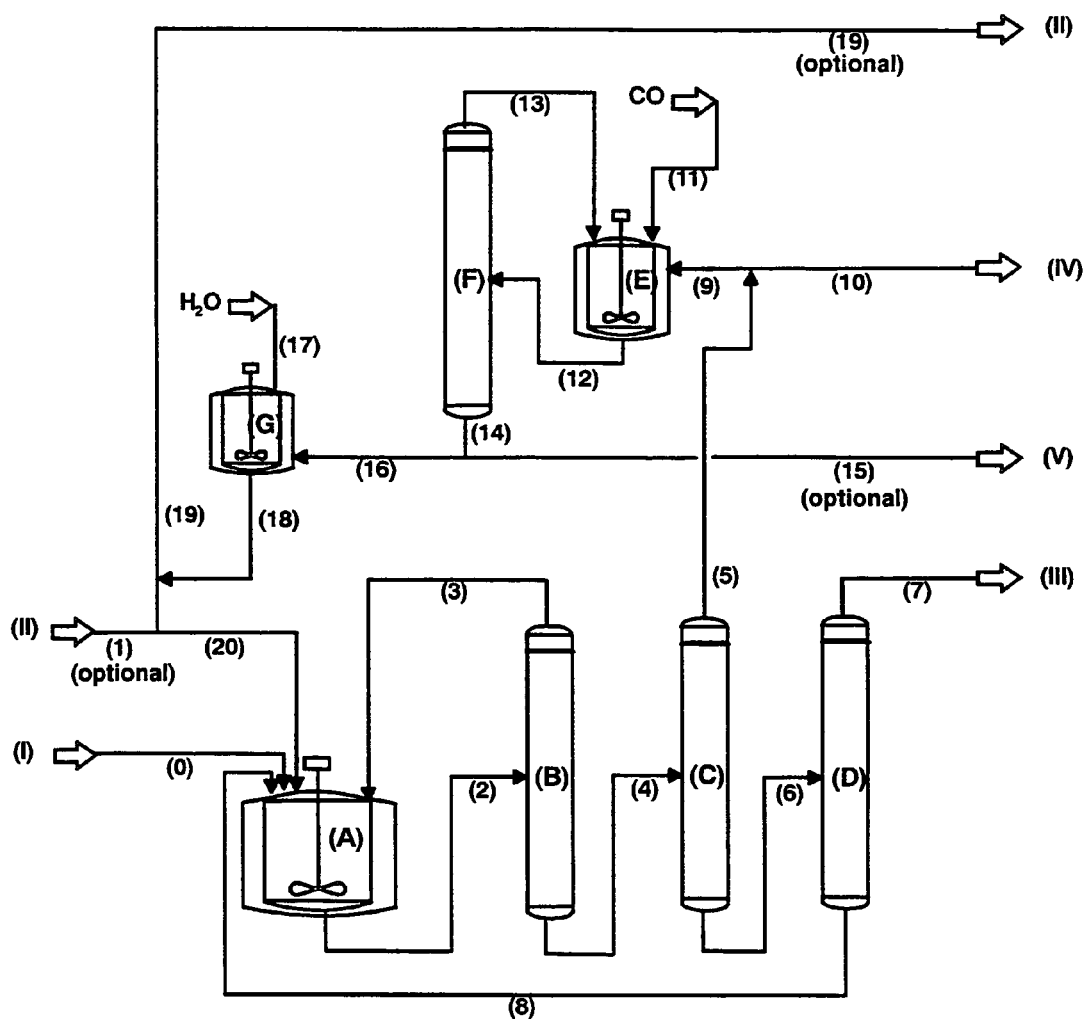
FIG. 4 shows a simplified process flow diagram for preparation of formic acid and methyl acetate (with acetic acid circuit).

A simplified process flow diagram is shown in FIG. 4. The acetic acid (II) fed to the reactor (A) via line (20) comes predominantly, preferably entirely, from the acetic acid circuit. However, addition of further acetic acid via line (1) is also possible if needed. The transesterification is carried out as described in embodiment 1, which is explicitly incorporated by reference at this point.

Part of the methyl acetate (IV) formed is taken off via line (10). The other part is passed via line (9) to the carbonylation. The carbonylation is carried out as described in embodiment 1, which is expressly incorporated by reference at this point. Line (15) makes it possible for carboxylic anhydride (V) to be discharged if desired.

Carboxylic anhydride (V) is conveyed via line (16) to the reactor (G), which is depicted by way of example as a stirred tank, where it is hydrolyzed. However, other suitable reaction apparatuses, for example those described above for step (c), hydrolysis (ii), can also be used as reactor (G). In the reactor (G), water (VIb) is introduced via line (17) and hydrolysis to acetic acid (II) takes place in the presence of the catalyst used. The reaction mixture, which comprises acetic acid (II) and the catalyst, is taken continuously from the reactor (G) and is generally freed of the catalyst in a further column (not shown in the interests of simplicity).

Acetic acid (II) can be taken off via the optional line (19) if desired.

The acetic acid (II) is recirculated via line (20) to the reactor (A), thus closing the loop.

Embodiment 3: Preparation of Formic Acid and Acetic Anhydride (with Acetic Acid Circuit)

Figure 5:
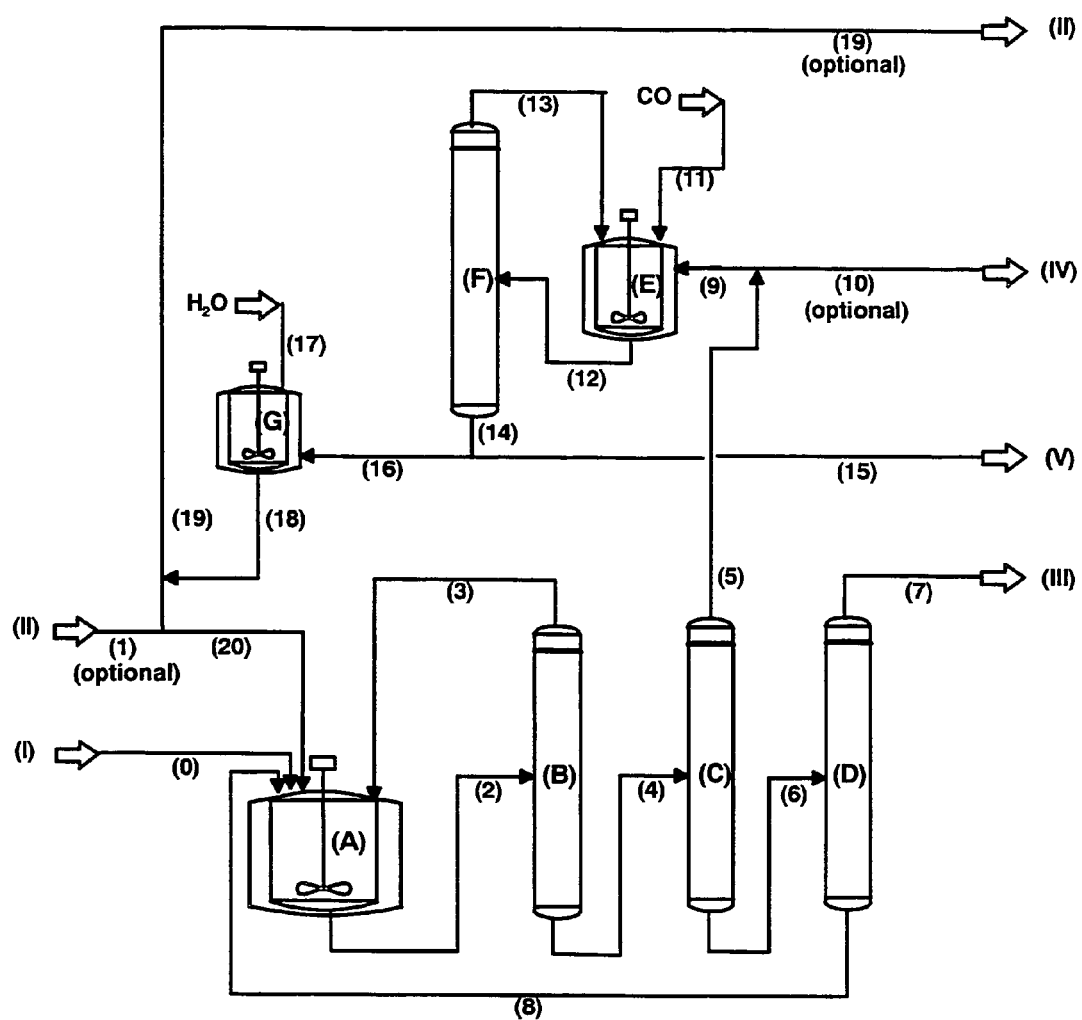
FIG. 5 shows a simplified process flow diagram for preparation of formic acid and acetic anhydride (with acetic acid circuit).

A simplified process flow diagram is shown in FIG. 5. The simplified process flow diagram corresponds essentially to that of embodiment 2, with part of the acetic anhydride (V) formed being taken off via line (15) and methyl acetate (IV) optionally being discharged via line (10). The other part of the acetic anhydride (V) is hydrolyzed in reactor (G) and returned to the reactor (A) via line (20), thus closing the loop.

Embodiment 4: Preparation of Formic Acid and Acetic Acid (with Acetic Acid Circuit)

Figure 6:
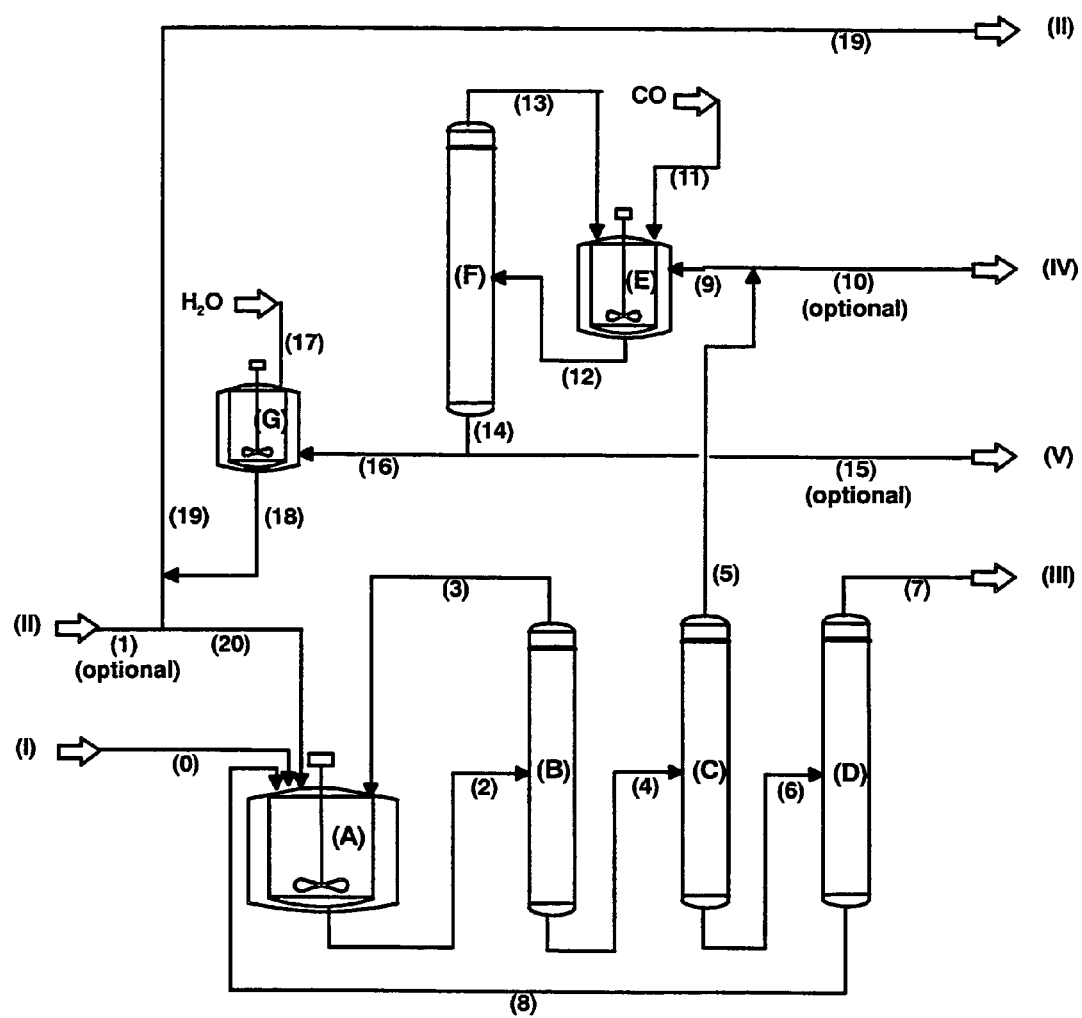
FIG. 6 shows a simplified process flow diagram for preparation of formic acid and acetic acid (with acetic acid circuit).

A simplified flow diagram is shown in FIG. 6. The simplified flow diagram corresponds essentially to that of embodiment 2, with part of the acetic acid (II) formed being taken off via line (19) and methyl acetate (IV) optionally being discharged via line (10). The other part of the acetic acid (II) is returned to the reactor (A) via line (20), thus closing the loop.

Embodiment 5: Preparation of Formic Acid and Ketene (with Acetic Acid Circuit)

Figure 7:
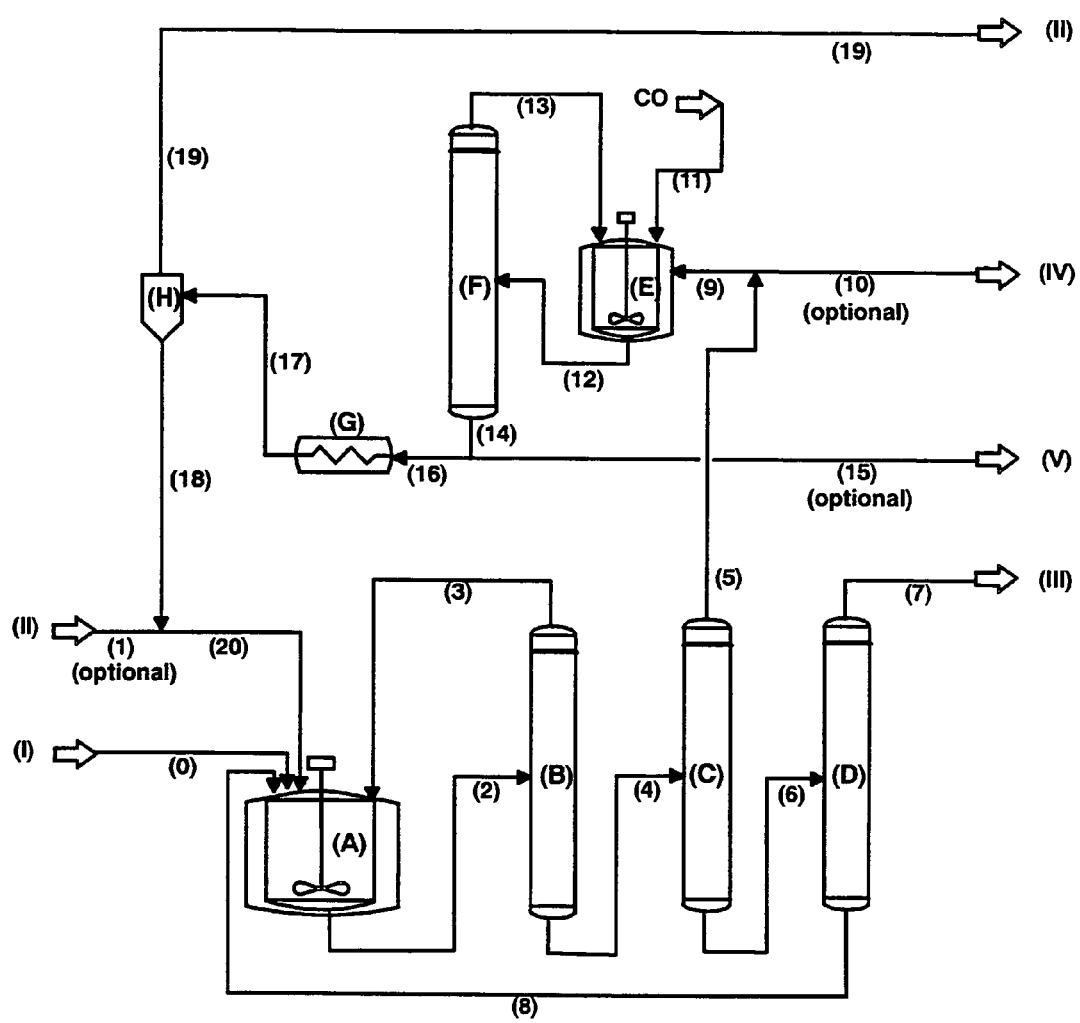
FIG. 7 shows a simplified process flow diagram for preparation of formic acid and ketene (with acetic acid circuit).

A simplified flow diagram is shown in FIG. 7. The part of the simplified flow diagram for the transesterification and the carbonylation corresponds to the part shown in embodiment 4. Part of the acetic anhydride (V) formed is conveyed via line (16) to the reactor (G) where it is thermally decomposed. As reactor (G), it is possible to use all suitable reaction apparatuses, for example those described above for step (c), thermal decomposition (i). The reaction gas formed, which comprises ketene (VIIa), acetic acid (II) and unreacted acetic anhydride (V), is conveyed via line (17) to the apparatus (H) for condensation and/or scrubbing. Ketene (VIIa) leaves apparatus (H) in gaseous form via line (19). The condensed stream is taken off via line (18) and is, for example, separated in a downstream column (not shown in the interests of simplicity) into acetic acid (II) and acetic anhydride (V), which may be recirculated to the reactor (G), or the condensed stream is hydrolyzed completely to acetic acid (II) in a downstream hydrolysis zone. The acetic acid (II) formed is conveyed via lines (18) and (20) back to the reactor (A), thus closing the loop.

Embodiment 6: Preparation of Formic Acid $C_1$–$C_4$-alkyl Acetate (with Acetic Acid Circuit)

Figure 8:
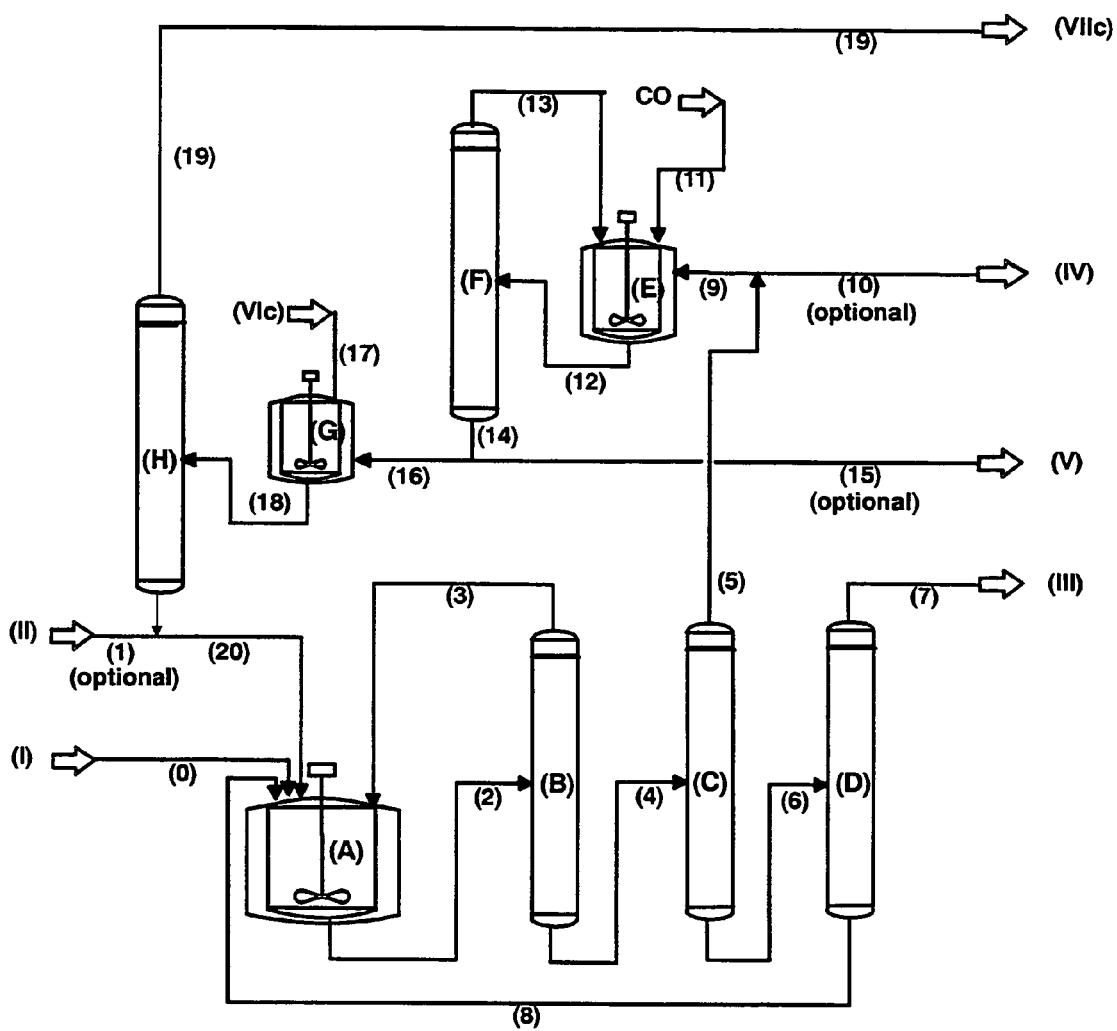
FIG. 8 shows a simplified process flow diagram for preparation of formic acid and $C_1$–$C_4$-alkyl acetate (with acetic acid circuit).

A simplified flow diagram is shown in FIG. 8. The part of the simplified flow diagram for the transesterification and the carbonylation corresponds to the part shown in embodiment 4. The acetic anhydride (V) formed is fed via line (16) to the reactor (G) for acylation (alcoholysis). As reactor (G), it is possible to use all suitable reaction apparatuses, for example those described above for step (c), use as acylating reagent (iii)–(aa). In the reactor (G), alcoholysis to acetic acid (II) and the $C_1$–$C_4$-alkyl acetate (VIIc) takes place in the presence of the catalyst used. $C_1$–$C_4$-alkanol (VIc) is continuously taken off via line (17). The reaction product, which comprises acetic acid (II), the $C_1$–$C_4$-alkyl acetate (VIIc), any unreacted acetic anhydride and the catalyst used, is generally freed of catalyst, for example in a flash evaporator (not shown in the interests of simplicity) and passed via line (18) to the column (H) for work-up by distillation. Here, the $C_1$–$C_4$-alkyl acetate (VIIc) is separated from the acetic acid (II) and taken off, depending on the relative boiling points, at the top (for example in the case of methyl, ethyl and propyl acetates) or at the bottom (for example in the case of butyl acetate). The stream comprising the $C_1$–$C_4$-alkyl acetate (VIIc) is discharged via line (19). The acetic acid (II) which has been separated off is returned to the reactor (A) via line (20), thus closing the loop.

Embodiment 7: Preparation of Formic Acid and Vinyl Acetate (with Acetic Acid Circuit)

Figure 9:
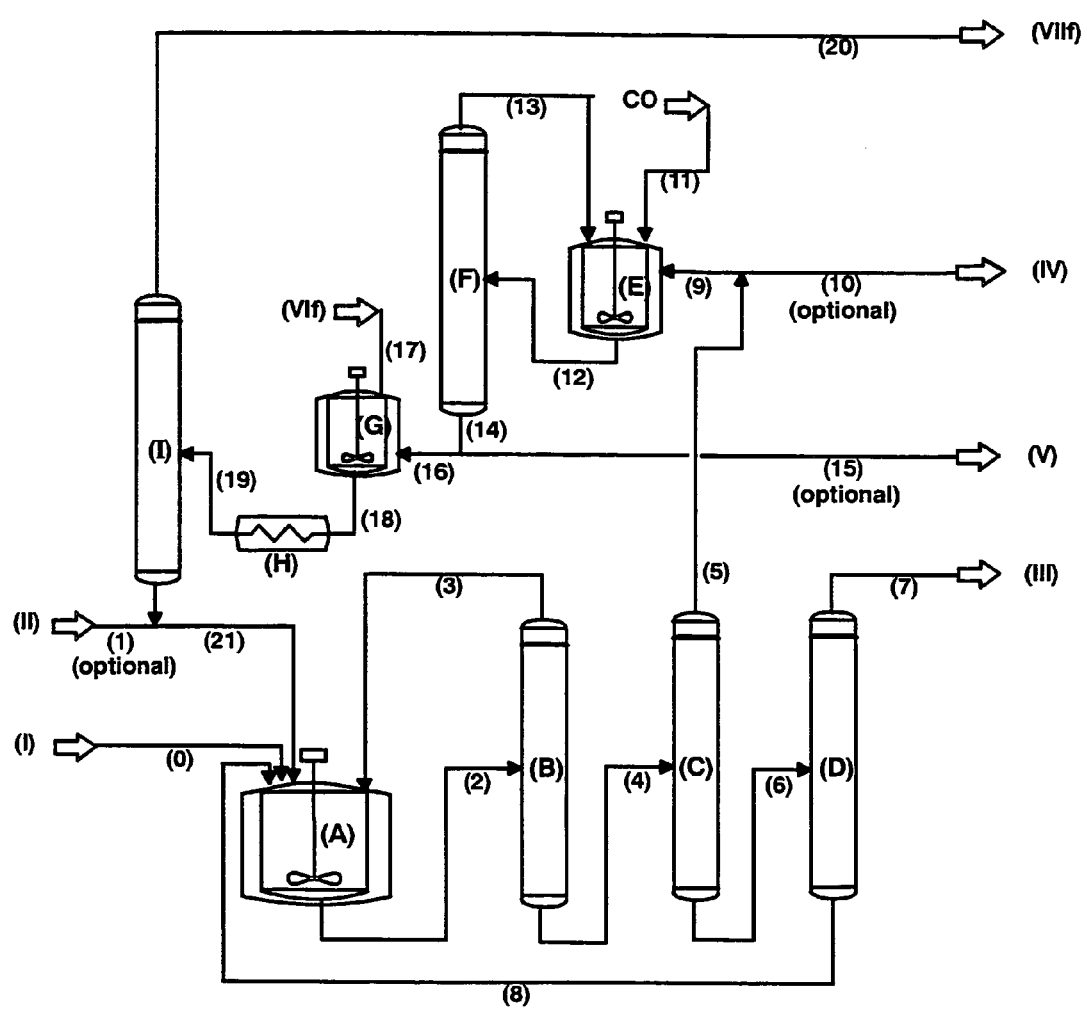
FIG. 9 shows a simplified process flow diagram for preparation of formic acid and vinyl acetate (with acetic acid circuit).

A simplified process flow diagram is shown in FIG. 9. The part of the simplified process flow diagram for the transesterification and the carbonylation corresponds to the part shown in embodiment 4. The acetic anhydride (V) shown is fed via line (16) to the reactor (G) for acylation (addition onto acetaldehyde). As reactor (G), it is possible to use all suitable reaction apparatuses, for example those described above for step (c), use as acylating reagent (iii)–(dd). In reactor (G), the addition reaction to form 1,2-diacetoxyethane (ethylene glycol diacetate) takes place in the presence of the catalyst used. For this purpose, acetaldehyde (VIf) is continuously fed in via line (17). The reaction product is continuously taken off via line (18) and passed to the reactor (H) where it is thermally decomposed. As reactor (H), it is possible to use all suitable reaction apparatuses, for example those described above for step (c), use as acylating reagent (iii)–(dd). The reaction mixture formed is condensed and/or scrubbed out and separated into vinyl acetate (VIIf) and acetic acid (II) in a further column (I). The vinyl acetate (VIIf) is taken off at the top and discharged as product via line (20). The acetic acid (II) separated off at the bottom is returned to the transesterification reactor, thus closing the loop.

Embodiment 8: Preparation of Formic Acid, Vinyl Acetate and Acetic Acid (with Acetic Acid Circuit)

The part of the process for the transesterification, the carbonylation and the acylation (alcoholysis using 1,2-ethanediol) corresponds essentially to the part shown in embodiment 6. The alcohol (VIc) used is 1,2-ethanediol (ethylene glycol). The reaction mixture produced in the alcoholysis step comprises essentially 1,2-diacetoxyethane and acetic acid (II). This is generally freed of acetic acid (II) by distillation and the 1,2-diacetoxyethane is passed to a thermolysis zone. The reaction mixture formed is condensed and/or scrubbed out and separated into vinyl acetate (VIIf) and acetic acid (II) in a further column. The vinyl acetate (VIIf) and part of the acetic acid (II) are taken off as product. The other part of the acetic acid (II) is returned to the transesterification reactor, thus closing the loop.

Embodiment 9: Preparation of Formic Acid and Vinyl Acetate (with Acetic Acid Circuit)

The part of the process for the transesterification and the carbonylation corresponds essentially to the part shown in embodiment 6. The acetic anhydride (V) formed is fed to the hydrogenation/thermolysis reactor where it is subjected to a reductive reaction. As reactor, it is possible to use all suitable reaction apparatuses, for example those described above for step (c), hydrogenation (iv). Hydrogen (VIh) and, if appropriate, carbon monoxide are fed into the reactor and the reaction to form vinyl acetate and acetic acid (II) takes place there in the presence of the catalyst used. The reaction mixture formed is generally separated into vinyl acetate and acetic acid (II) in a downstream column. The vinyl acetate is taken off as product. The acetic acid (II) is returned to the transesterification reactor, thus closing the loop.

Embodiment 10: Preparation of Formic Acid and Acetic Acid (with Acetic Acid Circuit and Simplified Separation of Methyl Formate and Acetic Acid)

Figure 10:
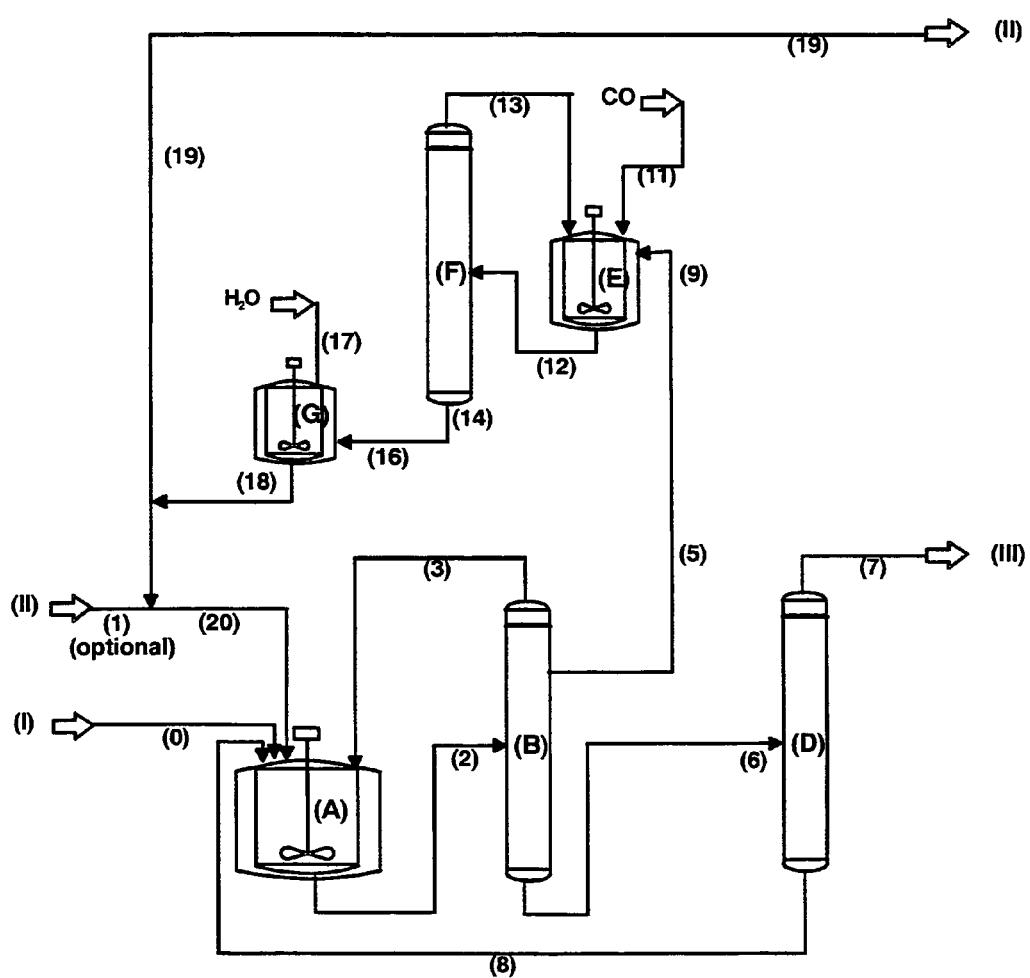
FIG. 10 shows a simplified process flow diagram for preparation of formic acid and acetic acid (with acetic acid circuit and simplified separation of methyl formate and acetic acid).

A simplified process flow diagram is shown in FIG. 10. Methyl formate (I) and acetic acid (II) are fed continuously into the reactor (A) via lines (0) and (20). The reaction mixture, which comprises methyl formate (I), acetic acid (II), formic acid (III), methyl acetate (IV) and the catalyst used, is taken continuously from the reactor (A) and conveyed via line (2) to the simplified work-up by distillation, which is depicted in the form of the columns (B) and (D). In column (B), the esters (I) and (IV) are separated from the acids (II) and (III), with the stream comprising the two acids being taken from the bottom of the column and conveyed via line (6) to the column (D). In column (D), the formic acid (III) is taken off at the top and discharged via line (7). Unreacted acetic acid (II), catalyst and any high boilers formed are returned via line (8) to the reactor (A). Methyl formate (I) and any low boilers formed are taken off at the top of the column (B) and returned via line (3) to the reactor. A stream comprising methyl acetate (IV) and methyl formate (I) is taken off from a side offtake in the absorption section of the column (B) and passed on via line (5). This generally comprises up to 300 mol % of methyl formate (I), based on methyl acetate (IV).

The stream comprising methyl acetate (IV) and methyl formate (I) is fed continuously to the reactor (E) via line (9).

In the reactor (E), the carbonylation of the methyl acetate (IV) to acetic anhydride (V) and the isomerization of the methyl formate (I) to acetic acid take place in the presence of the catalyst used. It should be emphasized that additional methyl formate (I) can be fed into the reactor (E) via a separate stream. The reaction mixture from reactor (E), which comprises unreacted methyl acetate (IV), unreacted methyl formate (I), the acetic anhydride (V) formed and the acetic acid formed and the catalyst used, is taken continuously from the reactor (E), generally freed of catalyst, for example in a flash evaporator (not shown in the interests of simplicity) and passed via line (12) to the work-up by distillation, which is depicted by way of example in the form of the column (F). The bottom product from the column (F), which comprises acetic anhydride (V), acetic acid and any high boilers formed, is taken off via line (14) and conveyed via line (16) to the reactor (G), which is depicted by way of example as a stirred tank, for hydrolysis. The low boilers are returned to the reactor via line (13). The acetic acid (II) from the hydrolysis reactor (G) is continuously discharged as product via line (19) and the amount of acetic acid (II) required for maintaining the circulation is conveyed via line (20) back to the reactor (A), thus closing the loop.

As an alternative, the bottom product from the column (F), which comprises acetic anhydride (V), acetic acid (II) and any high boilers formed, is separated in a further column into a stream comprising acetic acid (II) and a stream comprising the acetic anhydride (V) and any high boilers formed. The latter is fed to the hydrolysis reactor (G). The acetic acid (II) which has been separated off can then be fed to the reactor (A) for transesterification.

Embodiment 11: Preparation of Formic Acid and Acetic Anhydride with Acetic Acid Circuit and Simplified Separation of Methyl Formate and Acetic Acid)

Figure 11:
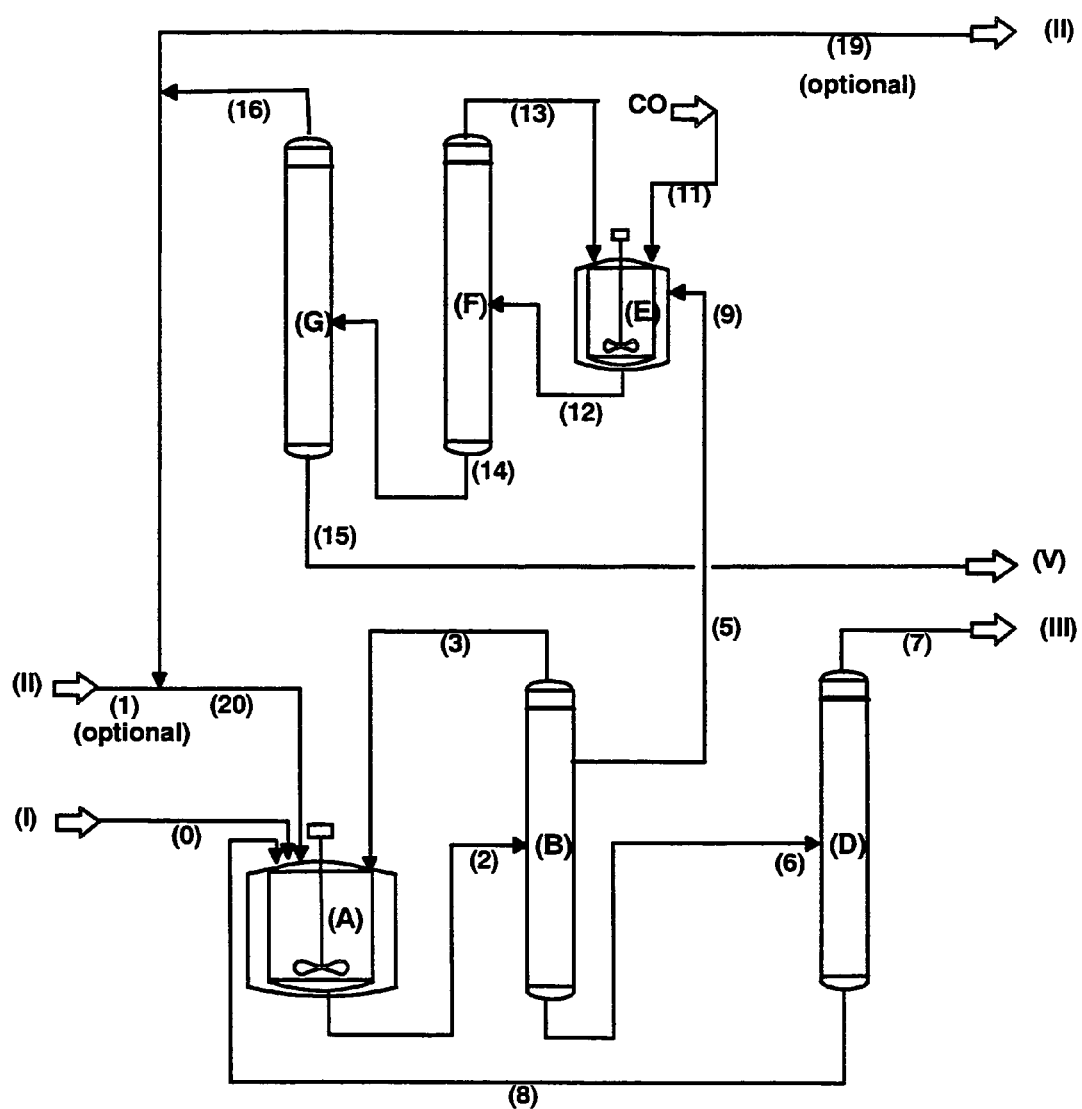
FIG. 11 shows a simplified process flow diagram for preparation of formic acid and acetic anhydride (with acetic acid circuit and simplified separation of methyl formate and acetic acid).

A simplified process flow diagram is shown in FIG. 11. The transesterification and the work-up of the reaction mixture are carried out as described in embodiment 10, to which explicit reference is made.

The stream comprising methyl acetate (IV) and methyl formate (I) is fed continuously to the reactor (E) via line (9). This stream generally comprises up to 300 mol % of methyl formate (I), based on methyl acetate (IV). In a very particularly preferred embodiment, this stream comprises the amount of methyl formate (I) which is necessary to produce the amount of acetic acid required for the acetic acid circuit. This corresponds to a stoichiometric content of 100 mol % of methyl formate (I), based on methyl acetate (IV), with the value to be set also being able to be higher or lower depending on possible losses. Thus, the acetic acid (II) required for maintaining the circulation is produced by transesterification of methyl formate (I).

The carbonylation and isomerization take place as described in embodiment 10, to which explicit reference is made. However, as a difference from embodiment 10, the bottom product from the column (F), which comprises acetic anhydride (V), acetic acid (II) and any high boilers formed, is conveyed via line (14) to the column (G) in which separation into a stream comprising acetic acid (II) and a stream comprising acetic anhydride (V) takes place. The acetic anhydride (V) is then discharged as product via line (15). The stream comprising acetic acid (II) is returned via lines (16) and (20) to the transesterification reactor (A). Depending on the amount of acetic acid formed, a further option is for some of it to be taken off via line (19).

As an alternative, it is also possible in this embodiment, for example, for additional methanol to be fed into the carbonylation reactor so as to achieve a further increase in the proportion of acetic acid. In a particularly preferred embodiment, the acetic acid required for maintaining the circulation is obtained by the isomerization of the methyl acetate and, if appropriate, by the carbonylation of additionally added methanol.

The process of the present invention makes it possible to prepare formic acid together with a carboxylic acid having at least two carbon atoms and/or derivatives thereof from readily obtainable and economically attractive raw materials. Thus, for example, the particularly preferred products formic acid, methyl acetate, acetic anhydride, acetic acid and ketene are based entirely on synthesis gas and thus on natural gas as raw material. In the case of the particularly preferred vinyl acetate, a total natural gas basis is likewise possible, for example, in the variant involving hydrogenation of the acetic anhydride. Depending on the origin of the ethanol, a total natural gas basis is also possible in the preparation of the particularly preferred ethyl acetate.

Furthermore, the process of the present invention makes possible a simple and inexpensive plant (low capital costs), a low energy consumption and low operating costs. As a result of the coupling of the production of formic acid and a carboxylic acid having at least two carbon atoms and/or derivatives thereof, a plant operating according to the process of the present invention has a significantly lower capital requirement than do two separate plants according to the prior art. In particular, the route via ketene, which is toxic and requires a high energy input for its production, is dispensed with in the preparation of acetic anhydride by the process of the present invention.

The process of the present invention avoids the formation of undesirable by-products resulting from coupled production.

In addition, the process of the present invention also makes it possible to prepare, if required, anhydrous formic acid and anhydrous carboxylic acids which are significantly less corrosive than the water-containing compounds and thus offer increased safety and make it possible to use cheaper materials of construction. The simple and economically attractive, compared to the prior art, route to anhydrous formic acid achieves a particularly high formic acid quality. The associated increase in the formic acid concentration to up to 100% also results in advantages in transport and storage.

Furthermore, the process of the present invention offers a high degree of flexibility in respect of the carboxylic acid having at least two carbon atoms and/or derivatives thereof, since the relative amounts of the compounds discharged can be varied within a wide range depending on requirements. The ratio of carbonylation products to formic acid can be increased by a further addition of an alcohol in the carbonylation stage. This results in a high degree of flexibility even in respect of additional production of carbonylation products and their downstream products.

In the preferred preparation of acetic acid and derivatives thereof, the process of the present invention offers the further advantage that the carbonylation of the methyl acetate can be carried out in the absence of water and a higher yield based on the carbon monoxide used compared to the industrially customary carbonylation of methanol can thus be achieved by avoidance of the water gas shift reaction.

TABLE 1

Preferred embodiments showing the idealized stoichiometric ratios.

| | Starting materials | Products | Process blocks |
|---|---|---|---|
| 1 | (I): Methyl formate<br>(II): Acetic acid<br>Carbon monoxide | (III): Formic acid<br>(V): Acetic anhydride | A, C |
| 2 | (I): Methyl formate<br>Carbon monoxide<br>(VI): Water | (III): Formic acid<br>(IV): Methyl acetate | A, B, C, E (hydrolysis)<br>Circulation of acetic acid (II) |
| 3 | (I): Methyl formate<br>Carbon monoxide<br>(VI): ½ Water | (III): Formic acid<br>(V): ½ acetic anhydride | A, C, D, E (Hydrolysis)<br>Circulation of acetic acid (II) |
| 4 | (I): Methyl formate<br>Carbon monoxide<br>(VI): Water | (III): Formic acid<br>(VI): Acetic acid | A, C, E (Hydrolysis), F<br>Circulation of acetic acid (II) |
| 5 | (I): Methyl formate<br>Carbon monoxide | (III): Formic acid<br>(VI): Ketene | A, C, E (thermal decomposition)<br>Circulation of acetic acid (II) |
| 6 | (I): Methyl formate<br>Carbon monoxide<br>(VI): $C_1$–$C_4$-alkanol | (III): Formic acid<br>(VI): $C_1$–$C_4$-alkyl acetate | A, C, E (Acylation)<br>Circulation of acetic acid (II) |
| 7 | (I): Methyl formate<br>Carbon monoxide<br>(VI): Acetaldehyde | (III): Formic acid<br>(VI): Vinyl acetate | A, C, E (Acylation)<br>Circulation of acetic acid (II) |
| 8 | (I): Methyl formate<br>Carbon monoxide<br>(VI): ½ 1,2-Ethanediol | (III): Formic acid<br>(VI): ½ Vinyl acetate + ½ acetic acid | A, C, E (Acylation)<br>Circulation of acetic acid (II) |
| 9 | (I): Methyl formate<br>Carbon monoxide<br>(VI): ½ Hydrogen | (III): Formic acid<br>(VI): ½ Vinyl acetate | A, C, E (Hydrogenation)<br>Circulation of acetic acid (II) |
| 10 | (I): Methyl formate<br>Carbon monoxide<br>(VI): Water | (III): Formic acid<br>(VI): n acetic acid | A, C, E (Hydrolysis), F<br>Circulation of acetic acid (II)<br>(n > 1) |
| 11 | (I): Methyl formate<br>Carbon monoxide<br>(VI): (2-n)/2 Water | (III): Formic acid<br>(VI): n/2 Acetic anhydride | A, C, D, E (Hydrolysis)<br>Circulation of acetic acid (II) (1 > n ≧ 2) |

We claim:

1. A process for the joint preparation of formic acid and a carboxylic acid having at least two carbon atoms and/or derivatives thereof, wherein
    (a) a formic ester is transesterified with a carboxylic acid having at least two carbon atoms to form formic acid and the corresponding carboxylic ester; and
    (b) at least part of the carboxylic ester formed in step (a) is carbonylated to give the corresponding carboxylic anhydride.

2. A process as claimed in claim 1, wherein
    (c) at least part of the carboxylic anhydride formed in step (b) is converted into the carboxylic acid.

3. A process as claimed in claim 2, wherein the carboxylic anhydride is converted into the carboxylic acid by thermal decomposition, by hydrolysis, by use as acylating reagent and/or by hydrogenation.

4. A process as claimed in claim 3, wherein the carbonylation of step (b) and the hydrolysis of step (c) are carried out together in one reaction apparatus.

5. A process as claimed in claim 3, wherein the carboxylic anhydride is used as acylating reagent in a reaction with an aldehyde or ketone to form an a,b-unsaturated carboxylic ester.

6. A process as claimed in claim 3, wherein the carboxylic anhydride is used as acylating reagent in a reaction with an alcohol to form a carboxylic ester.

7. A process as claimed in claim 3, wherein the carbonylation of step (b) and the hydrogenation of step (c) are carried out together in one reaction apparatus.

8. A process as claimed in claim 2, wherein at least part of the carboxylic acid formed in step (c) is used as starting material in step (a).

9. A process as claimed in claim 1, wherein the formic ester used is methyl formate.

10. A process as claimed in claim 1, wherein the carboxylic acid used is acetic acid.

11. A process as claimed in claim 9, wherein formic acid is prepared together with methyl acetate, acetic anhydride, acetic acid, ketene, vinyl acetate, ethyl acetate, propyl acetate and/or butyl acetate.

* * * * *